United States Patent
Baust

(10) Patent No.: US 12,042,203 B2
(45) Date of Patent: Jul. 23, 2024

(54) ENDOSCOPIC CRYOABLATION CATHETER

(71) Applicant: CPSI HOLDINGS LLC, Owego, NY (US)

(72) Inventor: John M. Baust, Candor, NY (US)

(73) Assignee: CPSI Holdings LLC, Owego, NY (US)

( * ) Notice: Subject to any disclaimer, the term of this patent is extended or adjusted under 35 U.S.C. 154(b) by 864 days.

(21) Appl. No.: 17/147,565

(22) Filed: Jan. 13, 2021

(65) Prior Publication Data

US 2021/0128220 A1     May 6, 2021

Related U.S. Application Data

(63) Continuation-in-part of application No. 15/881,441, filed on Jan. 26, 2018, now Pat. No. 10,918,432, which is a continuation-in-part of application No. 13/937,658, filed on Jul. 9, 2013, now Pat. No. 9,877,767.

(60) Provisional application No. 61/783,488, filed on Mar. 14, 2013.

(51) Int. Cl.
*A61B 18/02* (2006.01)
*A61B 18/00* (2006.01)
*A61B 18/14* (2006.01)

(52) U.S. Cl.
CPC .......... *A61B 18/02* (2013.01); *A61B 18/1492* (2013.01); *A61B 2018/00577* (2013.01); *A61B 2018/0212* (2013.01); *A61B 2018/0262* (2013.01)

(58) Field of Classification Search
CPC .. A61B 2018/0041; A61B 2018/00196; A61B 2018/00916; A61B 2018/00922; A61B 2018/00976; A61B 2018/00293
See application file for complete search history.

(56) References Cited

U.S. PATENT DOCUMENTS

| | | |
|---|---|---|
| 3,270,744 A | 9/1966 | Katz et al. |
| 3,859,986 A | 1/1975 | Okada et al. |
| 4,946,460 A * | 8/1990 | Merry .................... A61B 18/02 606/24 |
| 5,078,713 A | 1/1992 | Varney |
| 5,254,116 A | 10/1993 | Baust et al. |
| 5,281,213 A | 1/1994 | Milder et al. |

(Continued)

*Primary Examiner* — Ronald Hupczey, Jr.
(74) *Attorney, Agent, or Firm* — Hoffman Warnick LLC

(57) ABSTRACT

A cryoablation device is provide herein which, in an embodiment, includes a catheter shaft and a cryogen return line disposed within the catheter shaft. A cryogen supply line is disposed within the cryogen return line, such that the cryogen supply line, the cryogen return line, and the catheter shaft are all substantially coaxial. A needle tip probe is disposed at a distal end of the cryogen return line and the cryogen supply line extends in a distal direction beyond a distal end of the cryogen return line and into the needle tip probe. An insulating tube is disposed circumferentially around the cryogen return line and within the catheter shaft. An insulating lumen is circumferentially disposed around the return line, between an inner diameter of the catheter shaft and an outer diameter of the insulating tube. A position of the insulating tube is fixed relative to the catheter shaft. A position of the needle tip probe and the cryogen return line is axially and rotationally movable with respect to the insulating tube and the catheter shaft.

20 Claims, 16 Drawing Sheets

(56) References Cited

U.S. PATENT DOCUMENTS

| | | | |
|---|---|---|---|
| 6,551,309 B1* | 4/2003 | LePivert | A61B 18/02 606/23 |
| 6,786,902 B1* | 9/2004 | Rabin | A61B 90/17 606/22 |
| 6,974,455 B2 | 12/2005 | Garabedian et al. | |
| 8,915,908 B2* | 12/2014 | Privitera | A61B 18/02 606/21 |

* cited by examiner

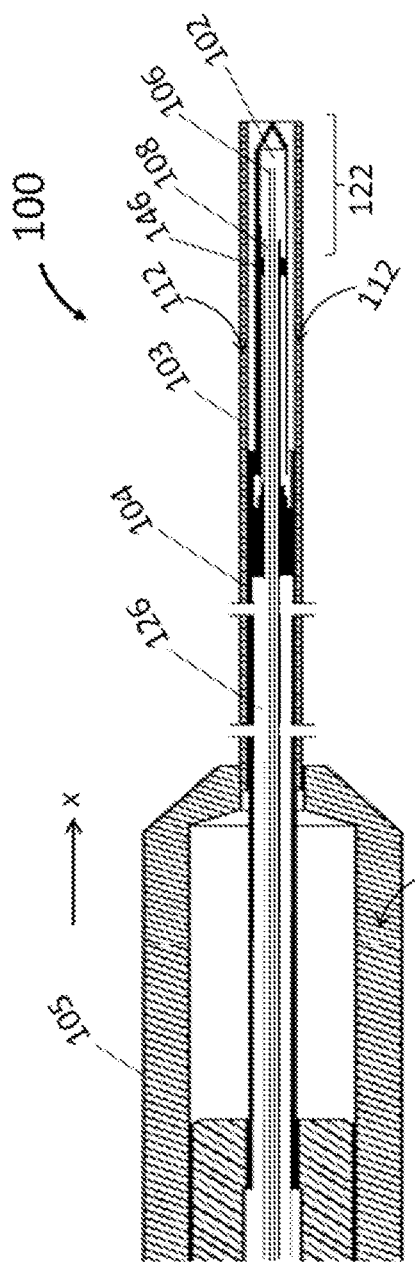
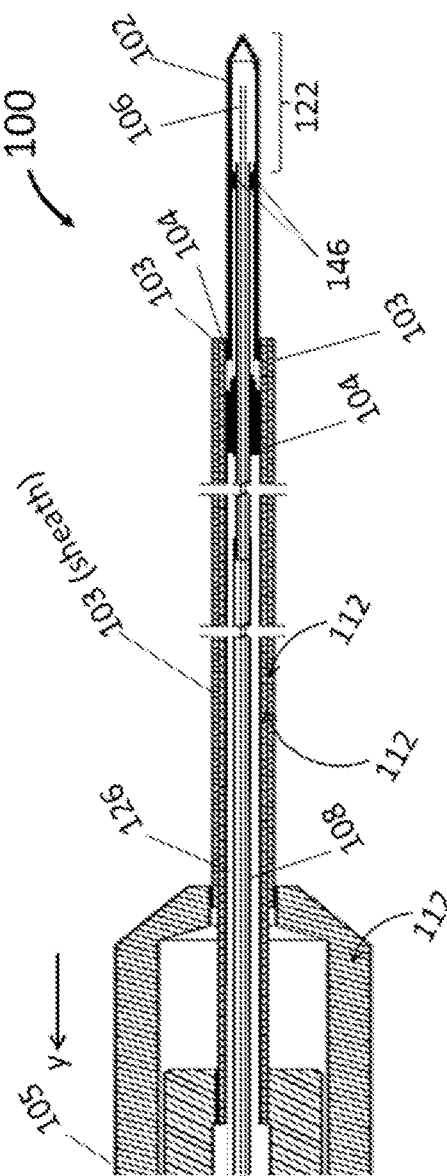

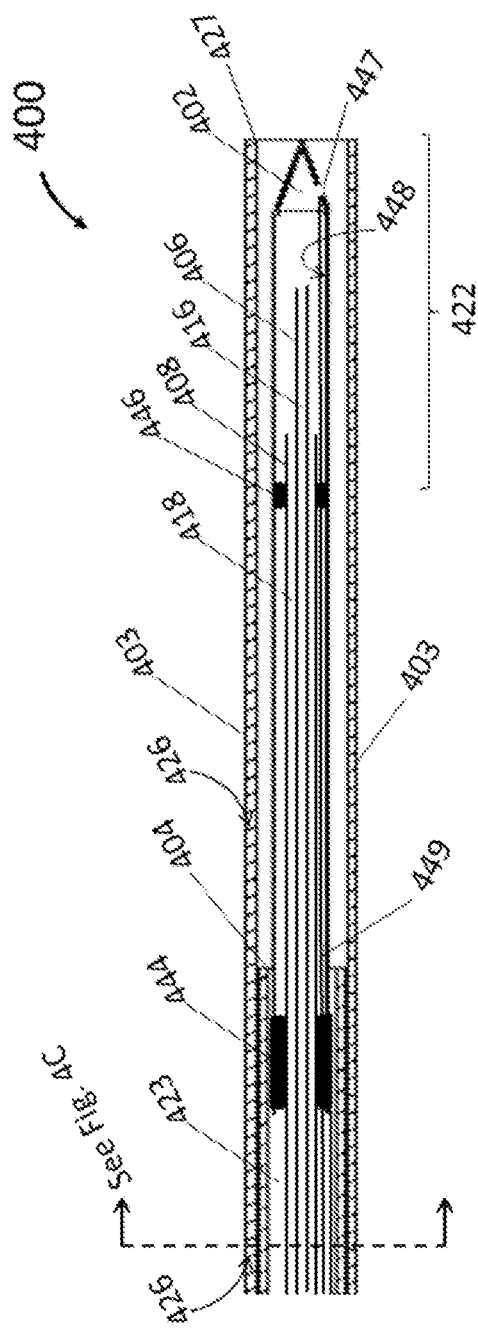
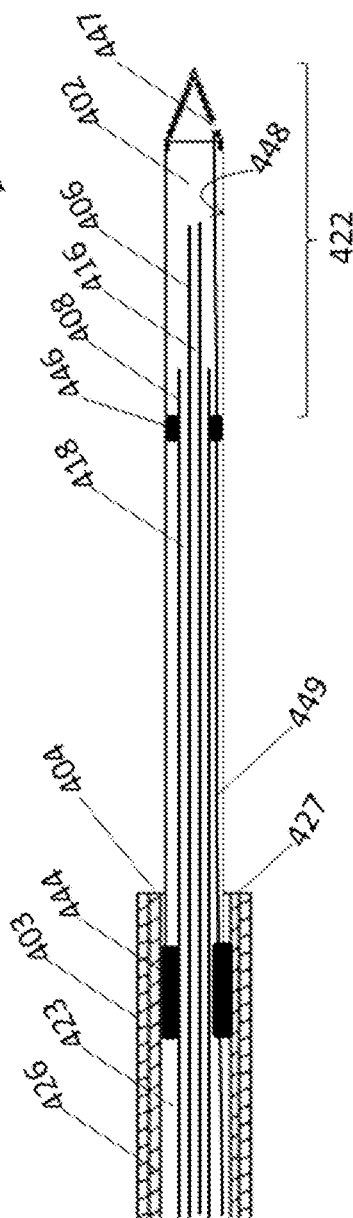
FIG. 4A
FIG. 4B

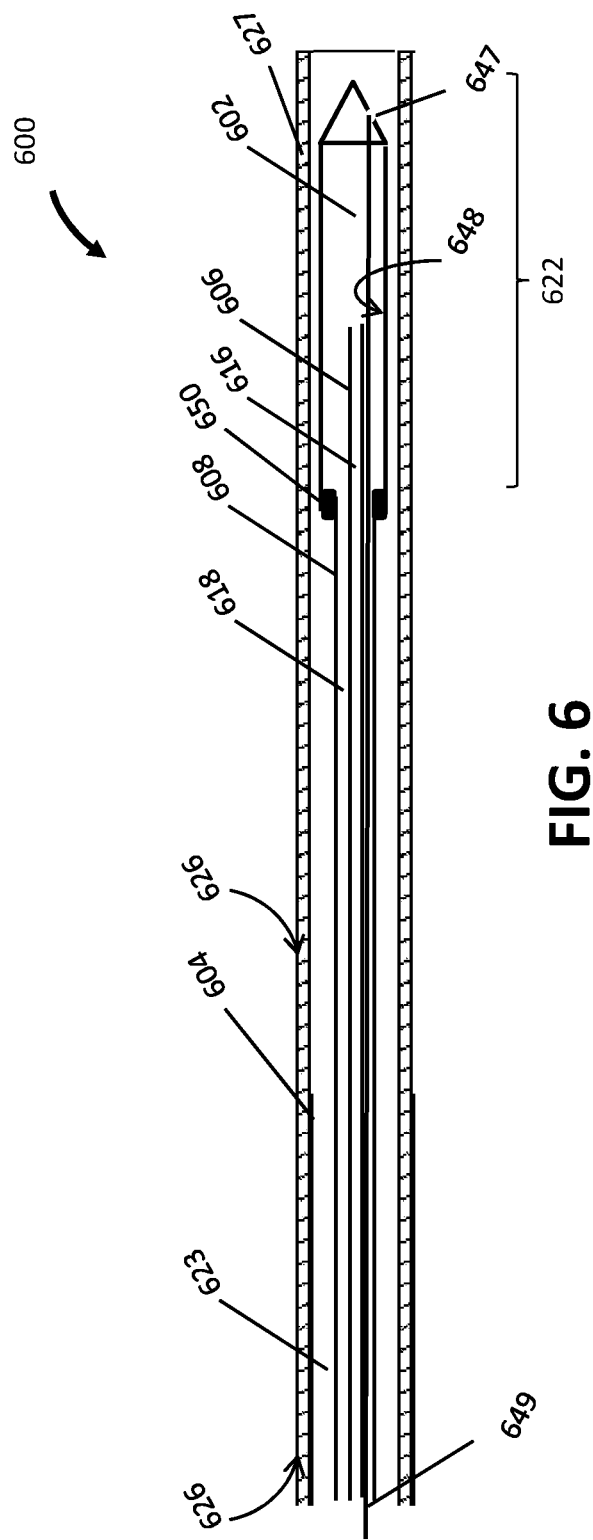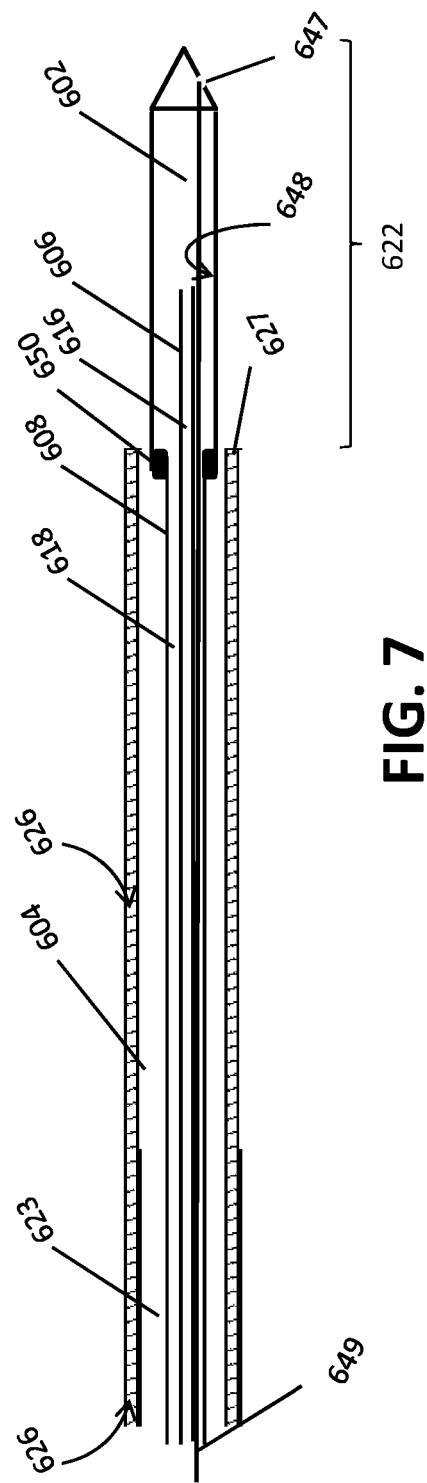

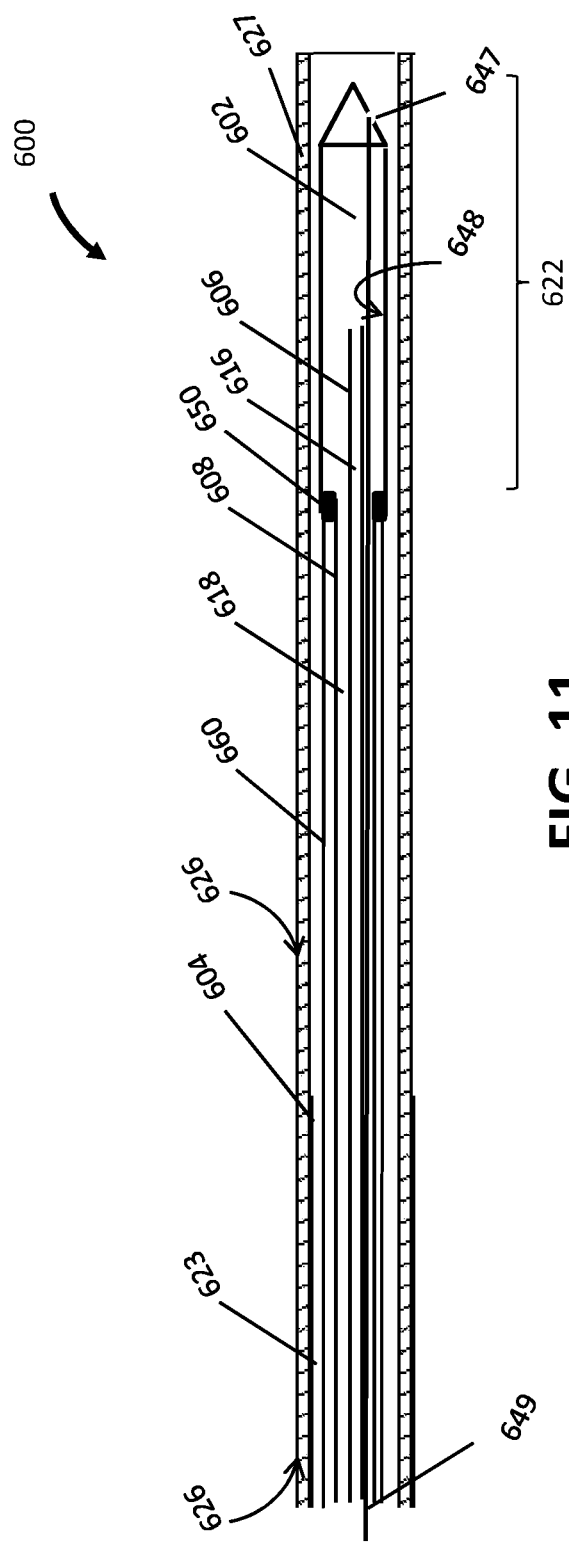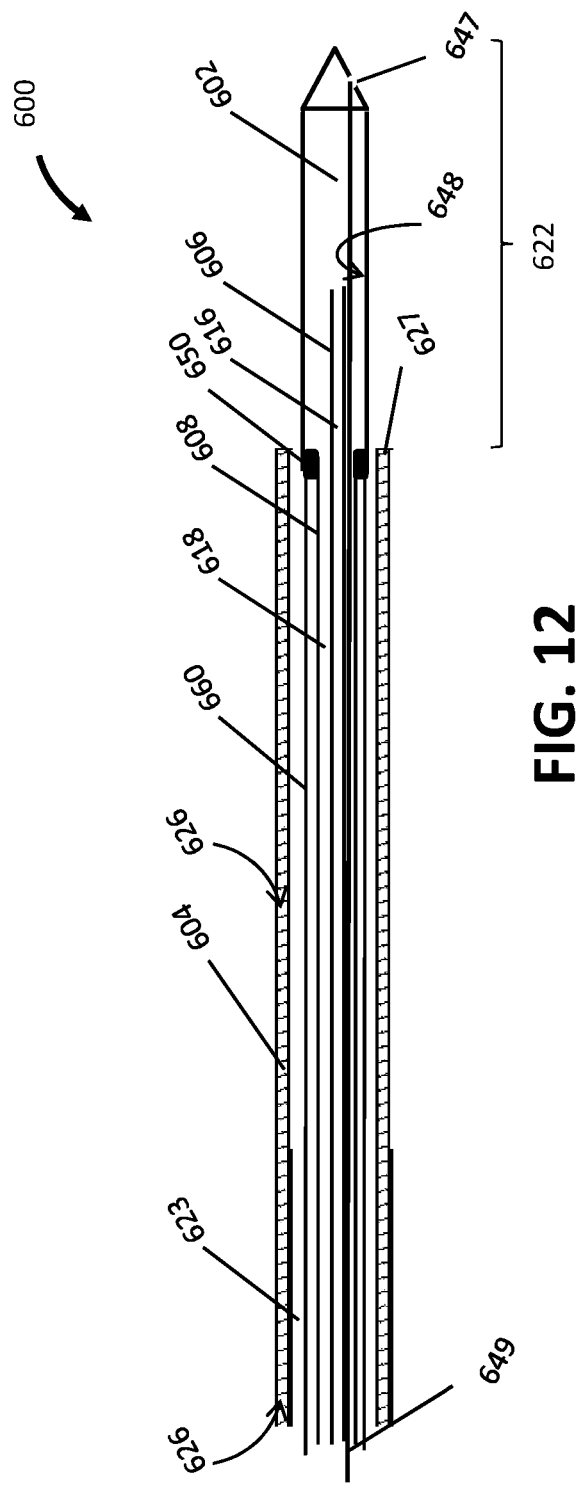

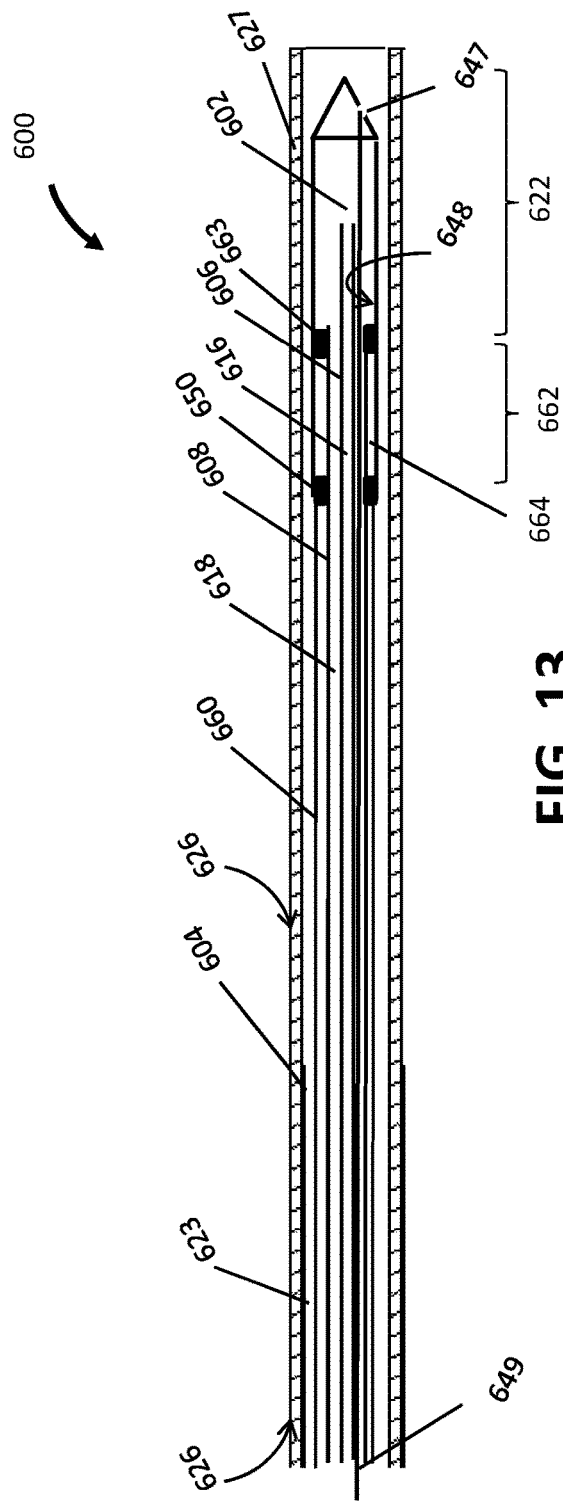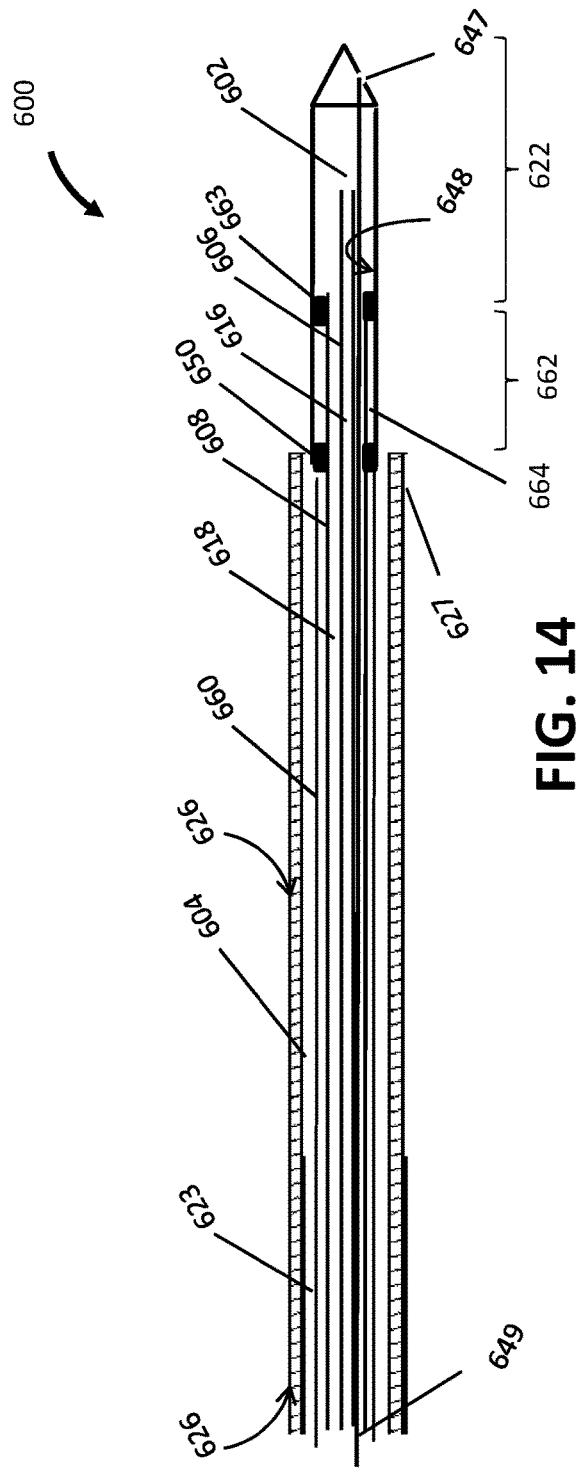

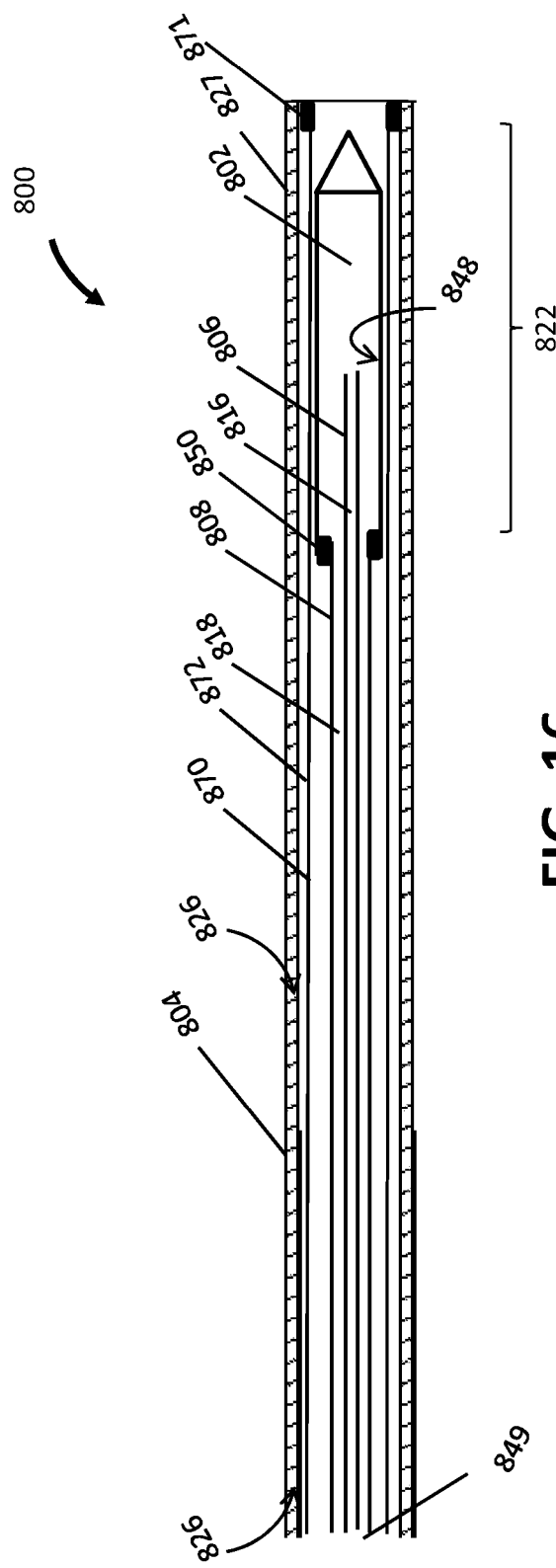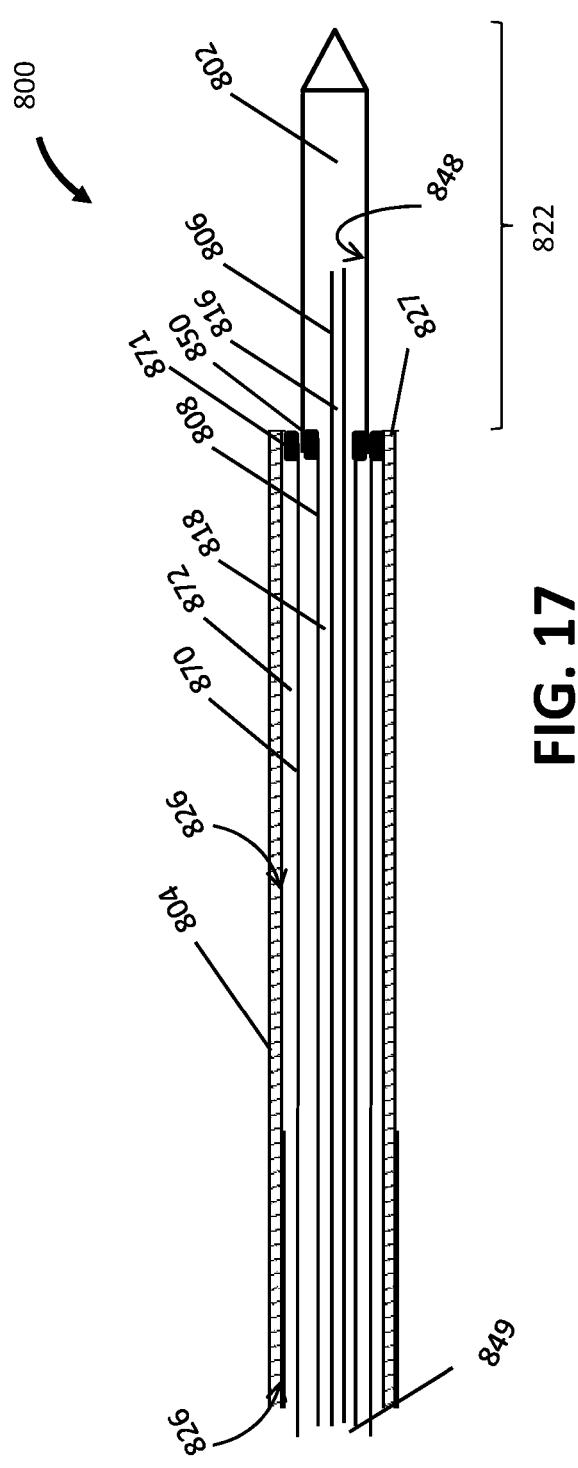

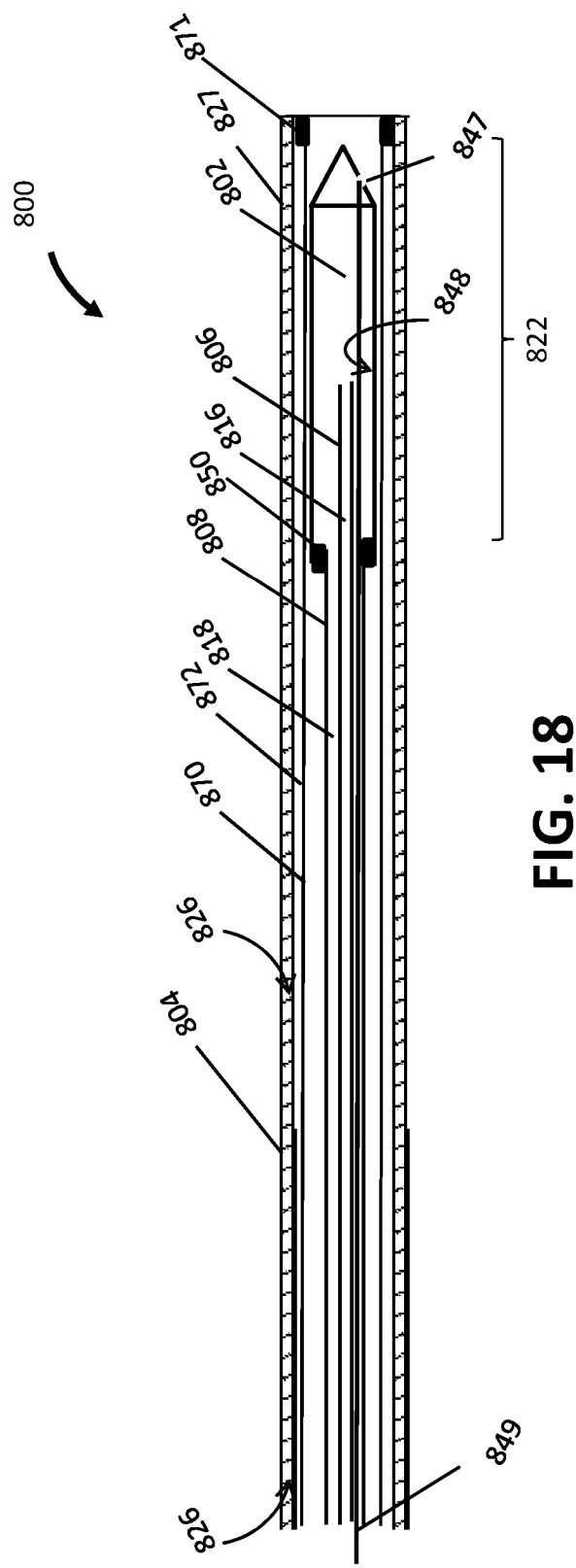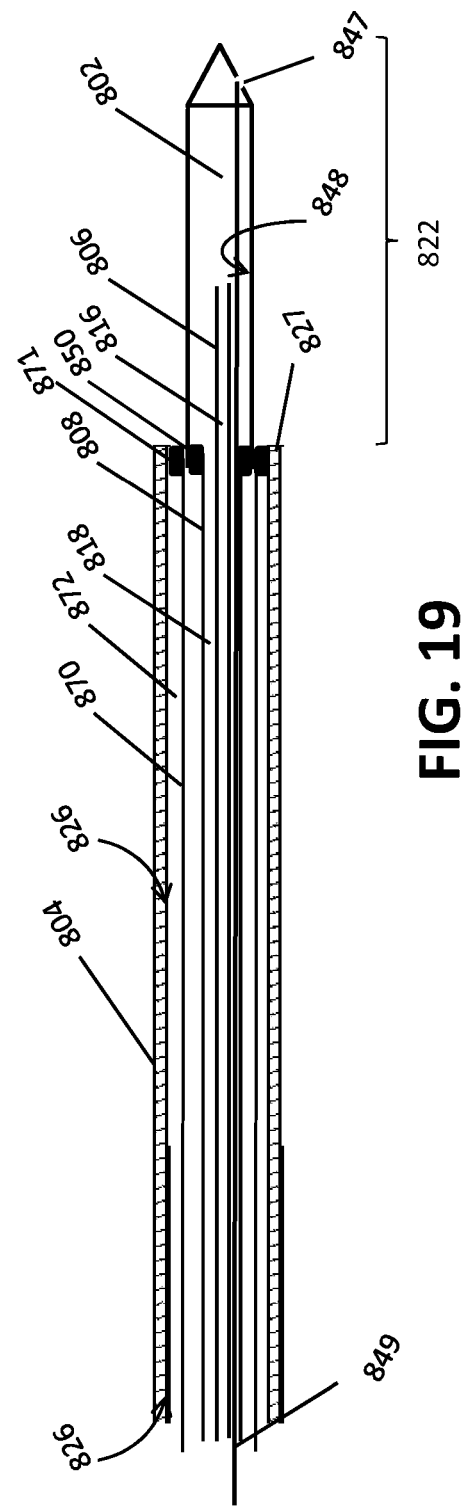

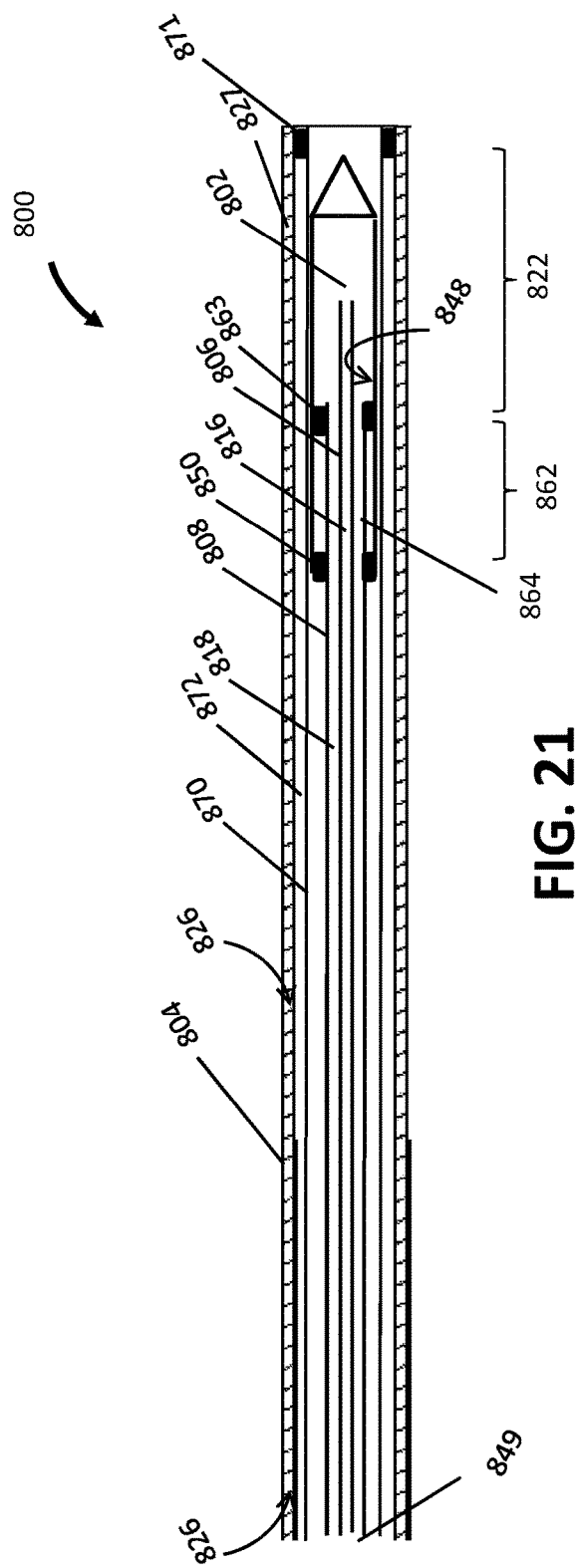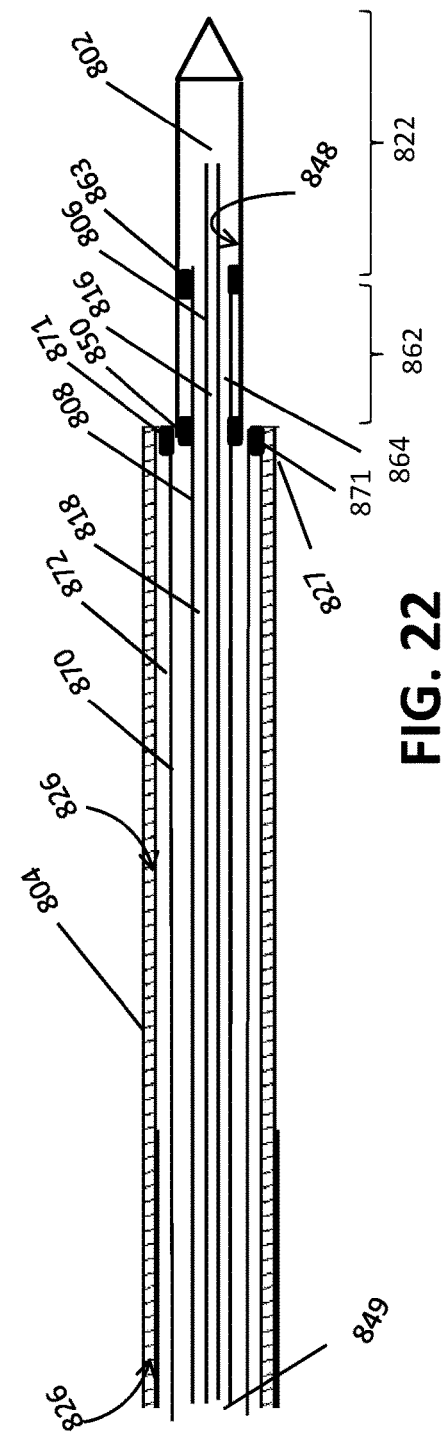
FIG. 21
FIG. 22

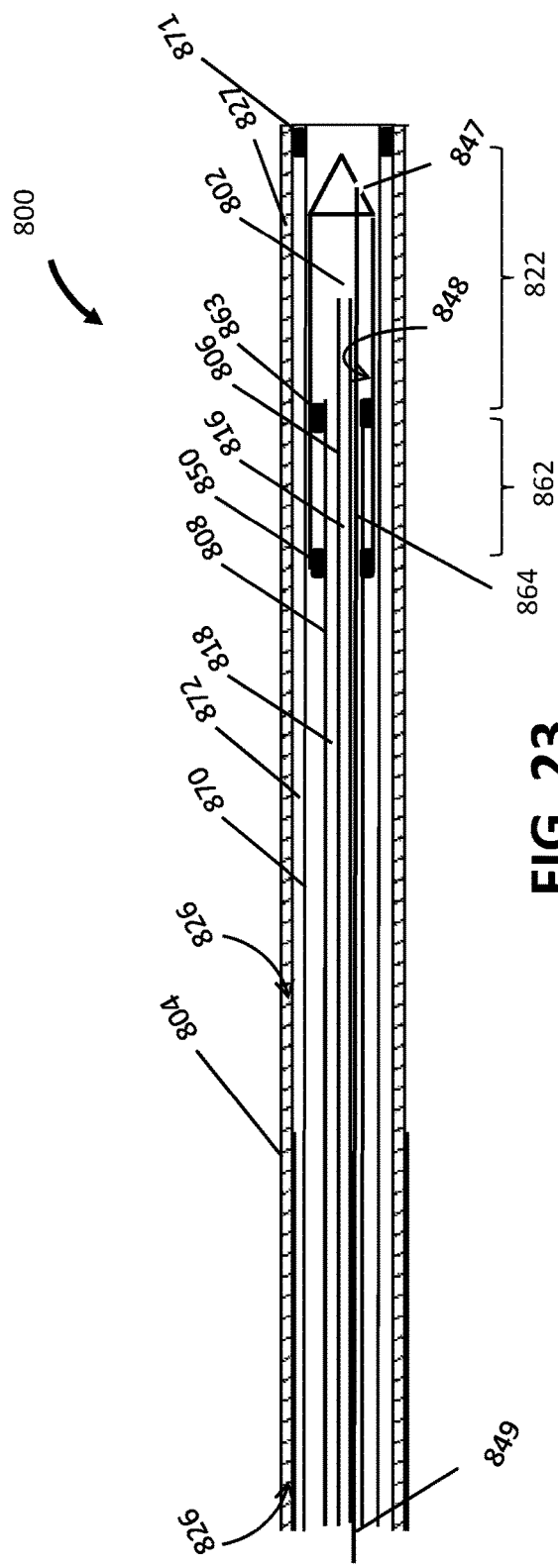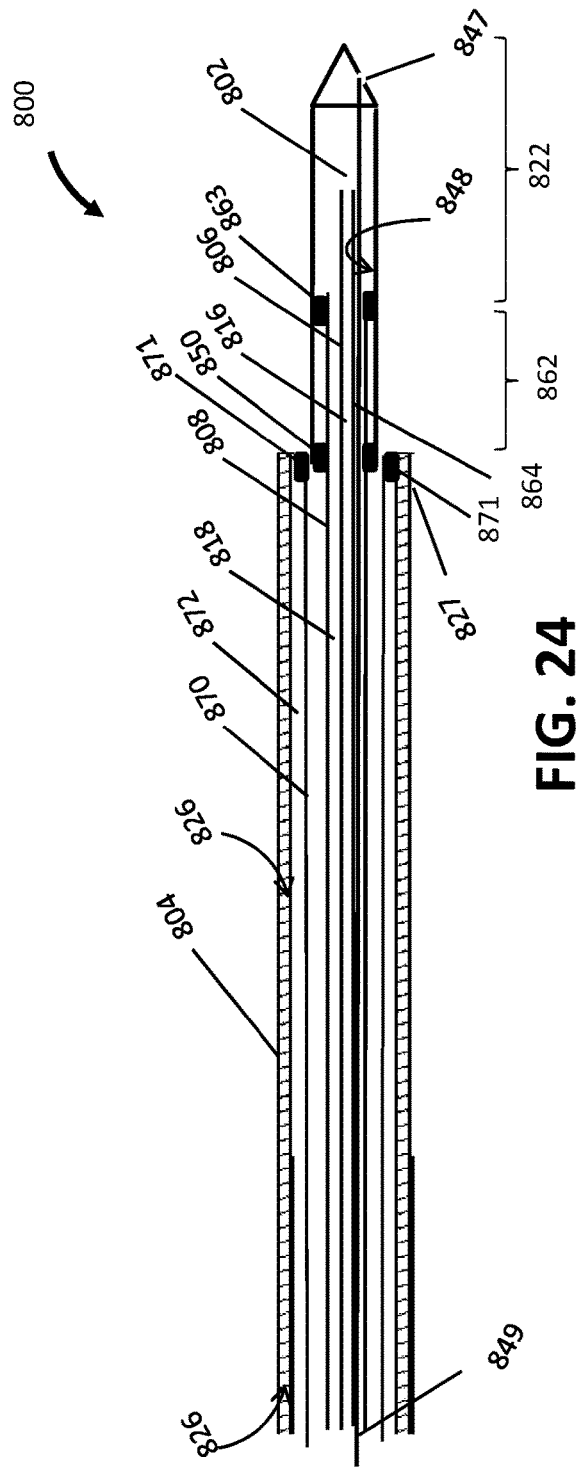

ENDOSCOPIC CRYOABLATION CATHETER

CROSS REFERENCE TO RELATED APPLICATIONS

The present application is a continuation-in-part of U.S. application Ser. No. 15/881,441, filed Jan. 26, 2018 and issued as U.S. Pat. No. 10,918,432 on Feb. 16, 2021, which was a continuation-in-part of U.S. application Ser. No. 13/937,658, filed Jul. 9, 2013 and issued as U.S. Pat. No. 9,877,767 on Jan. 30, 2018, which claims the benefit of U.S. Application No. 61/783,488, filed Mar. 14, 2013. Each of the foregoing US patent applications is incorporated by reference as though fully set forth herein.

FIELD OF THE INVENTION

The present invention relates generally to medical devices, and, in particular, to a surgical catheter for cryoablation.

BACKGROUND OF THE INVENTION

Pancreatic cancer is one of the major causes of cancer death in Western countries. In 2010, an estimated 43,140 new cases of pancreatic cancer were diagnosed in the United States with an expected five year survival rate of less than about 10%. In about 20% of patients with no metastases, tumor resection is not feasible because of vascular invasion, poor general health, or lacking surgical techniques. The standard treatment for these patients is chemotherapy followed by chemo-radiation therapy, which results in a median survival of eight to twelve months or less.

Current therapeutic options for unresectable pancreatic cancer include radiofrequency ablation (RFA) and cryotherapy. As utilized in the treatment of pancreatic cancer, RFA risks thermal injury to important structures such as the bile duct, the duodenum, and vessels close to the pancreas. A major limitation with RFA is difficulty in assessing the ablated zone by ultrasound, magnetic resonance imaging (MRI) or computed tomography (CT) scan. The poorly perfused pancreatic area also makes it difficult to visualize. Further, studies have demonstrated that radiologic follow-up after ablation could not distinguish inflammatory reactions of the tumor tissue from tumor growth or necrosis within the first four weeks.

Studies have shown the effective use of cryoablation to treat pancreatic cancer via laparoscopic or transcutaneous approach with reduced side effects. Yet, broad based clinical utilization has been limited by commercial devices that do not provide adequate cooling power to effectively treat the cancerous tissue. The invasive nature of surgical (open or laparoscopic) access to the target also remains an ongoing issue along with technological limitations.

In addition, current cryoprobes as used in an endoscopic procedure can cause damage to the endoscope due to freezing of the catheter shaft to the inside of the endoscope. This can interfere with the ultrasound imaging and readjusting or removing the cryoprobe from the tissue or endoscope in a timely manner. Prolonged procedures also can cause freezing of the endoscope to surrounding tissue resulting in damage to non-target tissues such as the esophagus, stomach wall, colon, intestine, rectum or other structure.

For visualization of current pancreatic procedures, endoscopic ultrasound (EUS) has been utilized to image the pancreas in real-time. Issues related to laparoscopic ablation techniques, however, make imaging difficult. For example, anatomical location of the pancreas makes it difficult to visualize and access without damaging other tissues.

SUMMARY OF THE INVENTION

A first aspect of the invention provides an endoscopic cryoablation device comprising a catheter shaft; a cryogen return line disposed within the catheter shaft; and a cryogen supply line disposed within the cryogen return line, such that the cryogen supply line, the cryogen return line, and the catheter shaft are all substantially coaxial. A needle tip probe is affixed to a distal end of the cryogen return line. The cryogen supply line extends in a distal direction beyond a distal end of the cryogen return line and into the needle tip probe, and the catheter shaft is axially movable relative to the needle tip probe and the cryogen return line, and the catheter shaft is configured such that the catheter shaft is distally extended over the needle tip probe in an extended position.

A second aspect of the invention provides an endoscopic cryoablation device comprising: a catheter shaft; a cryogen return line disposed within the catheter shaft; a cryogen supply line disposed within the cryogen return line, such that the cryogen supply line, the cryogen return line, and the catheter shaft are all substantially coaxial; and an insulating lumen circumferentially disposed around the return line, between an inner diameter of the catheter shaft and an outer diameter of the return line. A needle tip probe is disposed at a distal end of the cryogen return line, and the cryogen supply line extends in a distal direction beyond a distal end of the cryogen return line and into the needle tip probe.

A third aspect of the invention provides a cryoablation device comprising: a catheter shaft; a cryogen return line disposed within the catheter shaft; a cryogen supply line disposed within the cryogen return line, such that the cryogen supply line, the cryogen return line, and the catheter shaft are all substantially coaxial; a needle tip probe disposed at a distal end of the cryogen return line, wherein the cryogen supply line extends in a distal direction beyond a distal end of the cryogen return line and into the needle tip probe; an insulating tube disposed circumferentially around the cryogen return line and within the catheter shaft, and an insulating lumen circumferentially disposed around the return line, between an inner diameter of the catheter shaft and an outer diameter of the insulating tube, wherein a position of the insulating tube is fixed relative to the catheter shaft, and wherein a position of the needle tip probe and the cryogen return line is axially and rotationally movable with respect to the insulating tube and the catheter shaft.

Various aspects of the invention describe a cryoablation device integrated with an endoscope that facilitates rapid and effective treatment of pancreatic cancer or other gastrointestinal cancers or unwanted tissues.

In one embodiment, a cryoablation device provides a rapid and effective methodology to treat pancreatic cancer endoscopically. Endoscopic access in combination with targeted ablative techniques reduces procedure time, overall costs, and risks associated therewith. The improved endoscopic cryoablation device implements a cryoablation catheter compatible for use within an endoscope. The cryoablation catheter has the flexibility, stiffness, and steerability to place a probe tip located therein directly though the stomach wall and into a pancreatic tumor. The cryoablation catheter is also compatible with any other type of endoscope or colorectal scope for which its introduction and placement can be guided by any other type of visualization technique, including but not limited to external ultrasound, fluoroscopy, CT, MRI, optical and/or video assisted visualization. The sharp needle-like tip of the probe is capable of penetrating any desmoplasia, fibrous connective tissue, tumor infiltrate, and scar or fibrosis, even in patients who have already undergone radiation therapy. Additionally, the sharpness of this needle-like probe is utilized for EUS guided pseudocyst drainage during the procedure.

One embodiment of the endoscopic cryoablation catheter incorporates a cryoablation procedure which provides surgeons with a minimally invasive tool that reduces patient morbidity and lowers costs as compared to laparoscopic or surgical procedures. The method of using the apparatus for endoscopic ablation therapy comprises the steps of: providing an apparatus comprising a cryogen supply line and a cryogen return line surrounded by a catheter shaft, such that the cryogen supply line, the cryogen return line, and the catheter shaft run longitudinally from a proximal end at a cryogen console to a distal end at an ablation zone; wherein the distal end of the catheter shaft interconnects with a handle; inserting the catheter shaft into an endoscopic path, wherein the shaft covers the ablation zone; positioning the ablation zone to a tissue site; retracting the catheter shaft to expose the ablation zone; delivering cryogenic temperatures to the ablation zone for an allocated treatment time; allowing the ablation zone to thaw or heat; removing the ablation zone from the tissue site; protracting the sheath to cover the ablation zone; and removing the catheter shaft from the endoscopic path. In particular, the endoscopic cryoablation catheter is designed for use in treating pancreatic cancer in vivo. When positioning the ablation zone, or probe tip, the apparatus is directed through an endoscopic path that enters the stomach. The probe tip is a needle-tip probe that is inserted through a wall of the stomach and directed into the pancreatic tissue. Any number of procedures may be performed at a single treatment site or at various sites within or along an endoscopic path. Where a heating element such as a heating coil is utilized during thaw or active heat ablation, the tissue site can be further damaged. Further, the active heat ablation may be used to cauterize tissue at the treatment site or anywhere along the endoscopic path. As mentioned in detail in the following, any step during the procedure can be motorized, computerized, and/or programmed prior to, during, or following a procedure step in the methodology.

In one embodiment, the endoscopic cryoablation catheter is utilized in combination with other anti-cancer therapies including radiation, RF, chemotherapy, gene therapy, or any other treatment modality in simultaneous or staged delivery.

Furthermore, endoscopic access coupled with targeted in situ cancer destruction reduces procedure time, overall costs, and risks of complication while offering an effective therapeutic option currently unavailable to pancreatic cancer patients

BRIEF DESCRIPTION OF THE DRAWINGS

The accompanying drawings, which are incorporated in and constitute a part of this specification, illustrate various embodiments of the present invention, and, together with the description, serve to explain the principles of the invention. The various features are not necessarily drawn to scale. In fact, the dimensions may be arbitrarily increased or decreased for clarity of discussion. In the drawings:

FIG. 2 is a magnified transparent side view of a distal end of an embodiment of the invention with a covered probe tip.

FIG. 3 is a magnified transparent side view of a distal end of an embodiment of the invention with the cover sheath retracted.

FIG. 4A is magnified view of an embodiment of the invention such that the probe at the distal end is covered by the sheath.

FIG. 4B depicts an embodiment of the invention with the sheath retracted.

FIGS. 6-7 are illustrations of a device according to an embodiment of the invention, in the extended and retracted positions, respectively, including a needle-tip probe affixed to an outer wall of the cryogen return line, in an extended position.

FIGS. 11-12 are illustrations of a device according to an embodiment of the invention, in the extended and retracted positions respectively, including a needle-tip probe affixed to an inner wall of the return line, with an insulated tube disposed over the return line.

FIGS. 13-14 are illustrations of a device according to an embodiment of the invention, in extended and retracted positions respectively, including insulation disposed at a proximal end of the needle tip probe, and an insulated tube disposed about the return line.

FIGS. 16-17 are illustrations of a device according to an embodiment of the invention, in the extended and retracted positions, respectively, including a needle-tip probe affixed to an outer wall of the cryogen return line, and the return line and needle probe disposed within an insulated catheter shaft.

FIGS. 18-19 are illustrations of a device according to an embodiment of the invention, in the extended and retracted positions, respectively, including a needle-tip probe affixed to an outer wall of the cryogen return line, the return line, needle probe and accessory channel disposed within an insulated catheter shaft.

FIGS. 21-22 are illustrations of a device according to an embodiment of the invention, in the extended and retracted positions respectively, including a needle-tip probe affixed to an outer wall of the return line, with an insulated tube disposed around the return line wherein the insulative tube is affixed to the catheter.

FIGS. 23-24 are illustrations of a device according to an embodiment of the invention, in extended and retracted positions respectively, including insulation disposed at a proximal end of the needle tip probe, with an insulated tube disposed around the return line wherein the insulative tube is affixed to the catheter.

DETAILED DESCRIPTION

Disclosed herein is an endoscopic cryoablation apparatus for the ablation of undesirable tissue. A method of utilizing the endoscopic cryoablation apparatus to treat pancreatic cancer, gastrointestinal cancer, or other such tissue is also incorporated.

In describing the invention, reference will be made to various embodiments, examples of which are illustrated in the accompanying drawings. Wherever possible, the same or like reference numbers will be used throughout the drawings to refer to the same or like parts.

A. Cryoablation Catheters Having a Sheath

Figure 1:
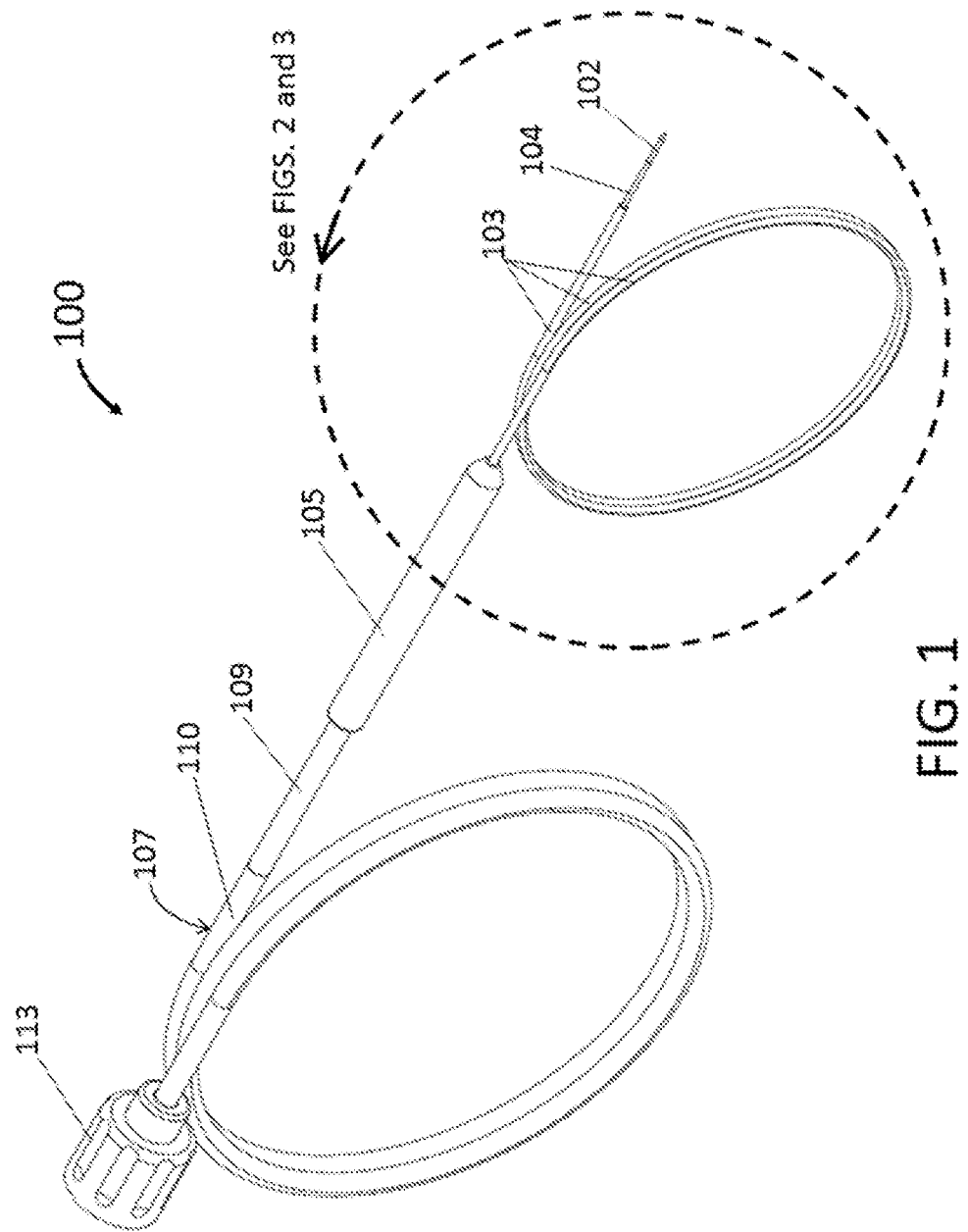
FIG. 1 is an external perspective view of an illustrative embodiment of the invention.

As illustrated in FIG. 1, the endoscopic cryoablation apparatus 100 comprises a cryoprobe tip 102 with an ablation zone 122 and integrated with a catheter shaft 104 such that a moveable sheath 103 covers and exposes the cryoprobe tip 102 by way of a controllable handle 105. As depicted, an umbilical 110 has an outer wall 107 and attaches to a connector 113 at a proximal end of the endoscopic cryoablation apparatus 100. The connector interconnects with a cryo-system, or cryogenic console (not depicted) to deliver cryogenic fluid to the cryoprobe tip 102. At a distal end, the cryoprobe tip 102 interconnects with a flexible catheter shaft 104. The flexible catheter shaft 104 has a polymeric composition with a diameter of between about 1 mm-5 mm, typically less than about 3.8 mm in diameter; and a length of between about 0.5 m-2 m, typically between about 0.5 m-1.5 m. The catheter shaft 104 can be safely passed through an operative channel of a therapeutic echoendoscope as desired. The overall longitudinal length of the apparatus 100 is between about 3 m to 6 m, or smaller, e.g., in the range of between about 1 m to 3 m. The diameter of the apparatus 100 varies along its longitudinal axis and may be between about 1 mm to about 10 mm, and even smaller, e.g., in the range of about 1 mm to about 3 mm.

In one embodiment, the catheter shaft 104 extends through the handle 105 and attaches to the umbilical 110 via retraction guide 109, which may be in the form of a transitional rigid portion. The retraction guide 109 may be plastic, and may be configured to attach the catheter shaft 104 to the umbilical 110. The handle 105 is fixed to move in the x-y directional plane across the retraction guide 109 but may also be capable of rotational movement around the catheter shaft 104 and retraction guide 109. A protective outer sheath 103 covers a distal end of the catheter shaft 104 between the handle 105 and a needle probe tip 102. The sheath 103 is open-ended at the distal end to expose the needle probe tip 102 for penetration into a target tissue when the sheath 103 is retracted. The sheath 103 interconnects with the handle 105 for synchronous control, movement and retraction. The retraction guide 109 assists in translational movement of the handle 105 to move the sheath 103 translationally along the x-y directional axis of the catheter shaft 104. The sheath extends a length of between about 1 m to about 2 m between the handle 105 and the probe tip 102, as dependent on the length of the catheter shaft from the probe tip 102 to the handle 105. The handle is typically about 10 cm in length with a diameter between about 1 mm to about 5 mm and larger so that a catheter of that size and dimension can be positioned within.

FIGS. 2 and 3 illustrate the distal end of the endoscopic cryoablation catheter 100 such that cryogen supply line 106 and cryogen return line 108 are housed in the catheter shaft 104. The catheter shaft is insulated by heating elements 112. A lumen 126 between the return line and catheter shaft provides an insulative layer to prevent freezing at an area external to the cryogen supply and return lines.

As shown in FIG. 2, the sheath 103 is protracted when the handle is moved or pushed toward the distal end of the apparatus 100 (as designated by the arrow 'x'). As shown in FIG. 3, retraction of the sheath exposes the probe tip 102 when the handle 105 is moved away from the distal end of the probe (as designated by the arrow 'y').

In addition, the catheter shaft 104 and umbilical 110 (see FIG. 1) are insulated throughout their respective lengths to prevent injury to nearby areas including anywhere along the endoscopic path, the region as defined by placement of the catheter shaft 104. For exemplary purposes, and not limitation, endoscopic paths may include passageways through the esophagus, stomach, endoscope or endoscopic lumen, visualization apparatus (e.g. EUS), or paths created by a physician's hand. As shown in FIGS. 2 and 3, the catheter shaft 104, outer sheath 103, and handle 105 include heating or defrosting elements 112 (as indicated by the hash marks) that prevent the shaft from freezing to an endoscope. The heating elements 112 comprise one or more electrically conductive wires integrated within the catheter shaft, sheath, and handle but may also include a mesh of heating wire to promote a more uniform heat distribution. Any configuration of wires may be utilized including, but not limited to, linear configurations, spiral arrangements of wires, or mesh formations. The heating elements 112 apply mild heat adjacent structures to prevent freezing, such as to prevent freezing between the catheter shaft 104 and the sheath 103, as well as between the catheter shaft 104 and tissue along the endoscopic path. The heating elements 112 reduce, and preferably eliminate, risk of damage to non-target tissue areas as well as to an independently operated endoscope.

For exemplary purposes only, and not limitation, the endoscopic cryocatheter or the independently operated endoscope may integrate an optical visualization tool, an ultrasound device, magnetic resonance imaging (MRI), computed tomography (CT), or any other visualization technique, alone or in combination, and with any compatible tool or technique.

Referring to FIGS. 2 and 3, the endoscopic cryocatheter 100 is insulated along the length of the shaft 104. This insulation is achieved by an insulative vacuum lumen 126 within the catheter shaft 104 upon which a vacuum is drawn. In FIG. 2, the probe tip 102 is covered by the sheath 103 (protracted configuration) when the handle is moved toward the distal end of the apparatus 100 (movement as indicated by the arrows). The probe tip and catheter are encased in the sheath 103 which covers the probe tip during catheter insertion to prevent damage to the endoscope, endoscopic cryocatheter 100, or puncture of tissue during endoscopic placement of the endoscopic cryocatheter 100 to an internal treatment site. In FIG. 3, the probe tip 102 is exposed when the handle 105 is moved towards the proximal end allowing the sheath 103 to retract at a tissue site designated for treatment. Additionally, any catheter or probe tip or configuration (needle, paddle, etc.) can be utilized and detachably affixed as long as it passes through the dimensions of the catheter shaft 104. When positioned to a treatment site through an endoscope (not illustrated), the sheath 103 is retracted to expose the ablation probe tip 102.

One embodiment of the probe tip 102 is illustrated as a needle-tip probe 102 capable of piercing a tissue. In one aspect, the needle-tip probe 102 is a sharp-pointed and stiff needle to penetrate the stomach wall and/or pancreatic parenchyma. The needle-tip probe 102 comprises an ablation zone, or freeze zone 122 at a far distal portion of the probe tip. The needle-tip probe 102 may be about 1.5 mm in diameter by about 4 cm, or may be up to about 15 cm in length, and may have an ablation zone of between about 10 mm-20 mm, or up to about 40 cm or longer. In some embodiments, the ablation zone may be about 12 mm to about 15 mm in length, dependent on the size of the needle tip probe. Any size, shape and dimension of needle can be utilized, as desired, depending on the tissue to be ablated. In addition, the probe tip 102 is compatible with a liquid or gas cryogen, or any cryogenic fluid, and allows the formation of ice at a tissue site. As such, the needle probe tip 102 is securely affixed to an internal wall of the catheter shaft 104 by a thermo-compatible adhesive. Thermal elements 146 in the probe tip 102 allow for thaw of the frozen tissue and release of the probe tip from the treated tissue (See depiction in FIGS. 2 and 3). The thermal elements 146 also act as spacers to maintain distance between the catheter shaft 104 and the supply and return lines. As illustrated here, the ablation zone 122 extends forward from the thermal elements 146 to the distal-most portion of the probe tip 102. Without limitation, the ablation zone may be created within any portion of the probe tip to integrate various portions, sizes, and dimensions as desired.

In another aspect, the sharp needle-like probe tip is capable of penetrating any desmoplasia, fibrous connective tissue, tumor infiltrate, and scar or fibrosis. Additionally, the sharpness of the needle-like probe tip can be used for EUS guided pseudocyst drainage during a procedure. The EUS cryoablation procedure provides surgeons with a minimally invasive tool that reduces morbidity and lowers costs.

In yet another aspect, the probe tip may be a blunt probe or catheter tip that forms an ablation zone at a focal point or along a linear path. Various embodiments of a probe tip may be incorporated herein without limitation.

One embodiment utilizes a catheter shaft 104 that interconnects with the probe tip 102 to provide continuous cryofluid delivery and return from the cryo-system. The connector 113 enables cryogen to run from the cryo-source at the proximal end of the apparatus 100 to the probe tip 102 at the distal end.

Figure 4C:
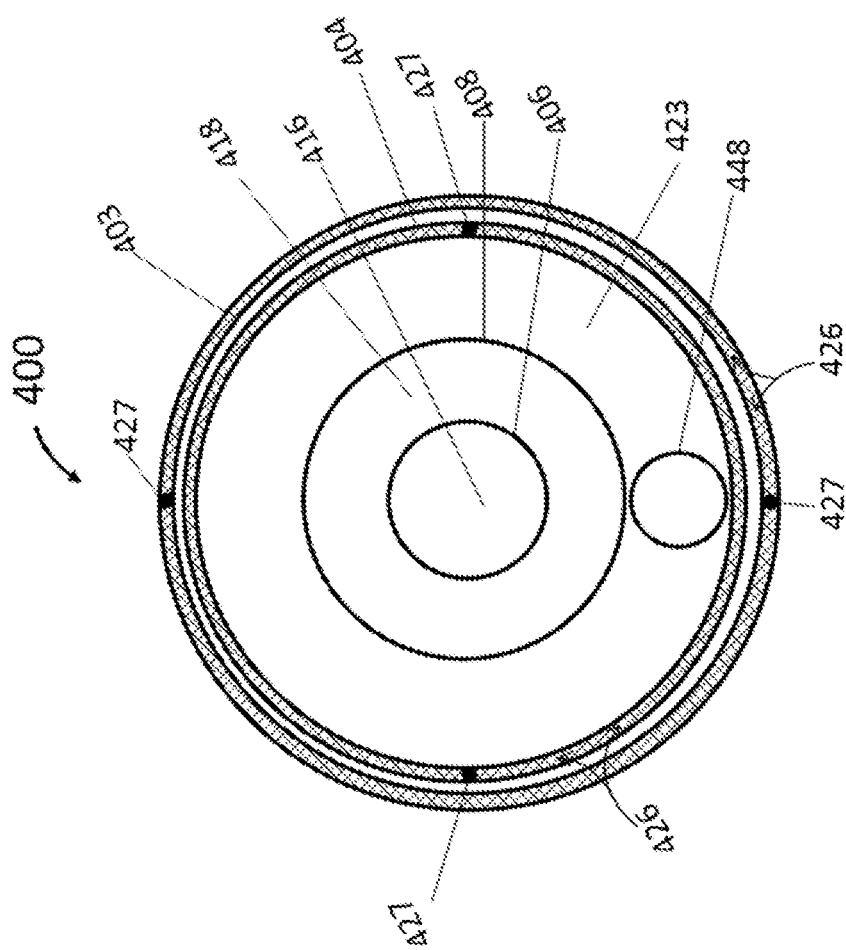
FIG. 4C is a cut-away cross section of an embodiment of the invention from FIG. 4A.

As depicted in FIGS. 4A and 4B, a distal end of an endoscopic cryoablation catheter 400 is magnified. A needle-tip probe 402 with an ablation zone 422 is connected to a catheter shaft 404 by way of an adhesive 444. Within the catheter shaft 404 is a supply line 406 defining a cryogen supply lumen 416 that runs longitudinally the length of the apparatus 400 and extends to a cryogen source at the console. The cryogen return line 408 circumferentially encases the supply line 406 such that a return lumen 418 is formed therebetween. Spacers 446 at the distal end of the needle-tip probe 402 maintain a space between the return line 408 and an inner surface 448 of the needle-tip probe. The supply line 406 and return line 408 run the length of the apparatus 400 (as similar to the invention as shown in FIG. 1). The coaxial design of cryogen supply line within the return line allows for more efficient use of space inside the catheter as compared to a side by side supply-return line design. Thus, the coaxial design provides catheter shafts having sizes as small as 0.5 mm or smaller; and catheter shafts can be manufactured up to about 1 cm or greater. In one aspect, the catheter shafts and probes can be interchanged depending on designated use in minimally invasive treatments and surgical, respectively. The catheter shaft 404 also creates an insulating lumen 423 to which an active or passive insulation can be applied. Active insulation is created when a vacuum is applied within the insulating lumen 423, or when heat is applied. Passive insulation allows gaseous components to occupy the insulating lumen 423, or where foam and other insulative materials are configured therein. See FIG. 4C which depicts a cut-away cross-section of FIG. 4A.

In the embodiment of the apparatus 400, as depicted in FIGS. 4A, 4B, and 4C, a thermal insulation 426 is utilized in both the catheter shaft 404 and the sheath 403. The thermal insulation 426 depicted includes an insulative thermoelectric mesh that integrates a plurality of electrical wires. The wire mesh uniformly insulates the catheter and sheath from cryogenic temperatures. The heat applied to the catheter shaft 404 and to the sheath 403 prevents freezing of the catheter and sheath while protecting endoscopic walls and cryocatheter components, and shielding tissues that are not designated for treatment. In another aspect, the thermal insulation may include one or more thermo-electric resistance wires in a linear arrangement, spiral, or mesh configuration.

As depicted in FIGS. 4A, 4B, and 4C, several electrical and mechanical deflection wires 427 are integrated within an internal wall of the catheter shaft 404 and sheath 403 to move and steer the distal end at the probe tip 402. In one aspect, the sheath is the steerable portion that integrates deflection wires 427 and directs the probe tip to the tissue site. In another aspect, the catheter shaft integrates the deflection wires 427 that direct the distal end to the tissue site. Deflection wires may be integrated along any wall of the longitudinal length of the apparatus and controlled via the handle controls or at a main console.

In one aspect, an accessory injection tube 449 is positioned within the insulating lumen 423 and extends longitudinally along the catheter shaft 404. The accessory injection tube 449 emerges at the distal end of a needle tip 402 at an exit portal 447. The accessory injection tube 449 allows for the introduction of drugs and therapeutic agents such as chemotherapeutic agents, gene therapy vectors and agents, hormones, vitamins, pro-apoptotic or anti-apoptotic agents, and clotting agents, for exemplary purposes and not limitation. The drugs and therapeutic agents can be introduced prior to, during and/or following an ablation procedure. Tissues and aspirate may also be withdrawn through the accessory tube 449.

Figure 5:
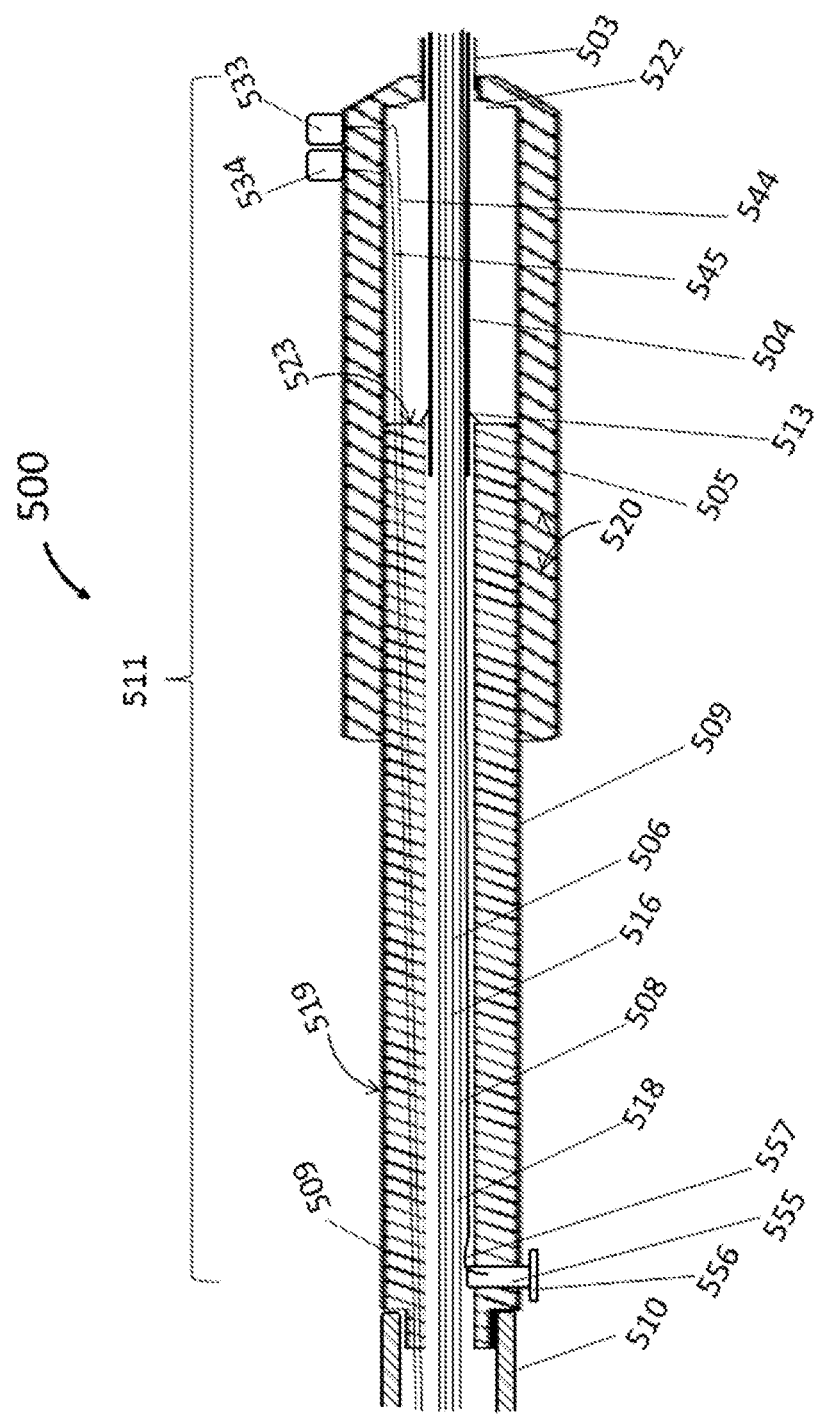
FIG. 5 is an embodiment of the invention with an internal view of the components in the handle portion.

An embodiment of the invention as shown in FIG. 5 illustrates a section of an endoscopic ablation catheter apparatus 500. Depicted is an umbilical 510 attached to a retraction guide 509. At an opposite end, a flexible catheter 504 is affixed to the retraction guide by adhesives 513 comprised of epoxy or cyanoacrylate adhesives, or other medical grade superglue. A handle 505 attaches to an outer sheath 503 at a distal end of the apparatus 500 such that the outer sheath 503 can be moved in the x-y directional axis as desired by the user. The handle 505 surrounds the catheter 504 and retraction guide 509 to form an integrated handheld portion 511. The handheld portion 511 also incorporates heating elements 520 to protect the user from cryo-temperatures generated within the device. As illustrated here, an internal forward stop 522 allows the handle 505 and sheath 503 to move back, synchronously, a pre-determined distance such that the handle covers a portion of the retraction guide 509. A reverse stop 523 of the retraction guide 509 allows the handle 505 and sheath 503 to be pushed forward a pre-determined distance over the catheter shaft 504. Distances can be indicated at 0.5 cm markings on the handle portion 511 to allocate the desired protraction and retraction of the sheath. Any desired increment, however, may be designated and marked. The markings allow the user to customize movement of the outer sheath 503 to a desirable location and keep record of the length of catheter shaft or probe tip exposed. Additionally, in some embodiments the sheath may be the limiting factor so as to designate the distance the handle is permitted to retract in which the sheath is not permitted to move beyond the larger diameter of the retraction guide.

As illustrated, a supply line 506 has an internal lumen 516 for delivery of cryogenic fluid to a probe tip. Return line 508 is positioned about the supply line to form a cylindrical lumen 518 disposed longitudinally with the supply line 506 throughout the length of the endoscopic cryoablation apparatus. Further, on/off controls 533 and 534 provide electrical connection 544 and 545, respectively, to allow the user to turn on/off the cryogen source, thaw, and/or heating elements 520. Other controls may be implemented to control gaseous discharge from the cryo-return lines, heating mechanisms throughout the length of the apparatus, temperatures adjustments, thermal monitoring, and visualization, among others. Automated operation of the apparatus may also be incorporated with the use of software based systems. In one aspect, automated control mechanisms also operate the sheath, individually or in combination with the handle. Further, the controls of the invention can be motorized for gradual precise positioning, as well as computerized to operate protraction and retraction of the sheath in synchrony with the handle. Any number of components of the invention may be motorized, computerized, and programmed as desired. Where the endoscopic cryocatheter is programmed, specific patient parameters may be integrated with a software program to facilitate placement of the probe tip, temperature adjustments, and treatment durations.

In another aspect, as shown in FIG. 5, the endoscopic cryoablation catheter 500 comprises an injection channel 555, access port 556, and accessory tube 557 for administering drugs, adjuvants, and therapeutic agents at the target tissue site. The access port 556 is a rigid twist lock within the handheld portion 511, but may also be a flexible tube to allow introduction of an agent via a syringe or similar mechanism. The access port 556 is positioned on an outer wall 519 of the retraction guide 509 but may be positioned anywhere in the handle portion 511 or along the length of the umbilical 510 or catheter shaft 504. The injection channel 555 allows entry of the agent into the accessory tube 557; the accessory tube 557 then runs longitudinally the length of the catheter shaft 504 to the distal end at the probe tip. An exit portal (not depicted here) within the needle tip seals a terminal portion of the accessory tube 557 to the needle tip to prevent any cryogen leaking from the needle tip probe. The accessory tube 557 is configured adjacent to the return line 508, within or along the catheter shaft 504 to allow for the introduction of additional adjuvants and agents as used in therapies such as chemotherapy, gene therapy, hormone and vitamin therapies. Such agents may include chemotherapeutic agents, gene therapy vectors, hormones, vitamins, pro-apoptotic or anti-apoptotic agents, and clotting agents, among others. The agents may be introduced at any stage of the procedure, including before, during, or after an ablation procedure. This accessory channel 557, along with the injection channel 555 and access port 556 can also be utilized for the introduction of biopsy needle apparatus, aspiration of fluid or tissue, or other device as desired. Additionally, the introduction of other ablative devices such as RF, high frequency ultrasound (HiFU), laser, or other ablative energies can be introduced. These channels within or along the endoscopic cryocatheter allow for the application of multiple treatment modalities to more effectively destroy the target tissue.

Further, in another aspect, the flexible endoscopic catheter of the invention may integrate any ablative device within the internal lumen of the catheter so as to advantageously allow for a plurality of treatment modalities through an integral tube. The consolidation of ablation devices minimizes invasiveness in patient treatment as well as treatment times and duration of the overall procedure.

In one embodiment, the catheter assembly, including supply and return lines encompassed in a catheter shaft, is contained in a sheath which slides freely over the outer surface of the catheter shaft allowing for the covering and uncovering of the probe tip during insertion and retraction of the endoscopic cryocatheter. In another embodiment, a portion of the catheter assembly is positioned over the freely sliding sheath. The sheath may comprise an insulative heating element along a portion or entire length of the catheter shaft to prevent freezing between the cryocatheter assembly and a wall of an endoscope. Any portion of the catheter shaft or the entire shaft can include the heating elements or insulative materials. The sheath terminates at the handle of the cryocatheter assembly and is affixed to the handle wherein movement of the handle and sheath sub-assembly causes movement of the sheath forward and backward to cover or uncover the probe tip, respectively. The components may be individually attached and affixed via adhesive or injection molded to form an integral component, or integral handle and sheath sub-assembly. The cryogen supply and return lines continue through the handle and through the umbilical to the connector where the coaxial lines diverge into independent cryogen supply and return lines. The connector compatibly aligns and seals with a connection of a cryogen source console.

In addition, between the cryogen return line and the umbilical is a lumen in which a vacuum or other type of insulation can be applied. This provides additional insulation to prevent freezing between components of the apparatus. Within or along the umbilical, control lines and electrical wires to control thawing, thermal monitoring, sheath movement, catheter tip steering, and accessory channels may be contained. The lines may run in a secondary umbilical parallel to that of the cryogen lines if so desired. This configuration separates the electromechanical control lines from that of the cryolines, while providing a reduced overall device size and footprint.

B. Cryoablation Catheters Without a Sheath

Turning to FIGS. 6-14, these figures illustrate various embodiments in which, in contrast with the foregoing embodiments, needle-tip probe 602 is affixed at joint 650 to the distal end of return line 608 within catheter shaft 604. Joint 650 may use adhesive such as, e.g., glue, to adhere needle tip probe 602 to return line 608. In these embodiments, needle-tip probe 602 is axially moveable in relation to the surrounding catheter shaft 604. Catheter shaft 604 may also be rotationally movable around needle-tip probe 602 and return line 608.

Aside from the absence of the sheath, and differences in actuation of needle probe tip 602 with respect to catheter shaft 604, device 600 of FIGS. 6-14 operates substantially similarly to devices 100/400/500 of FIGS. 1-5, respectively. Specifically, any feature described above with respect to device 100/400/500 may also be combined with device 600. Any such combinations are omitted only in the interest of brevity.

Figure 8:
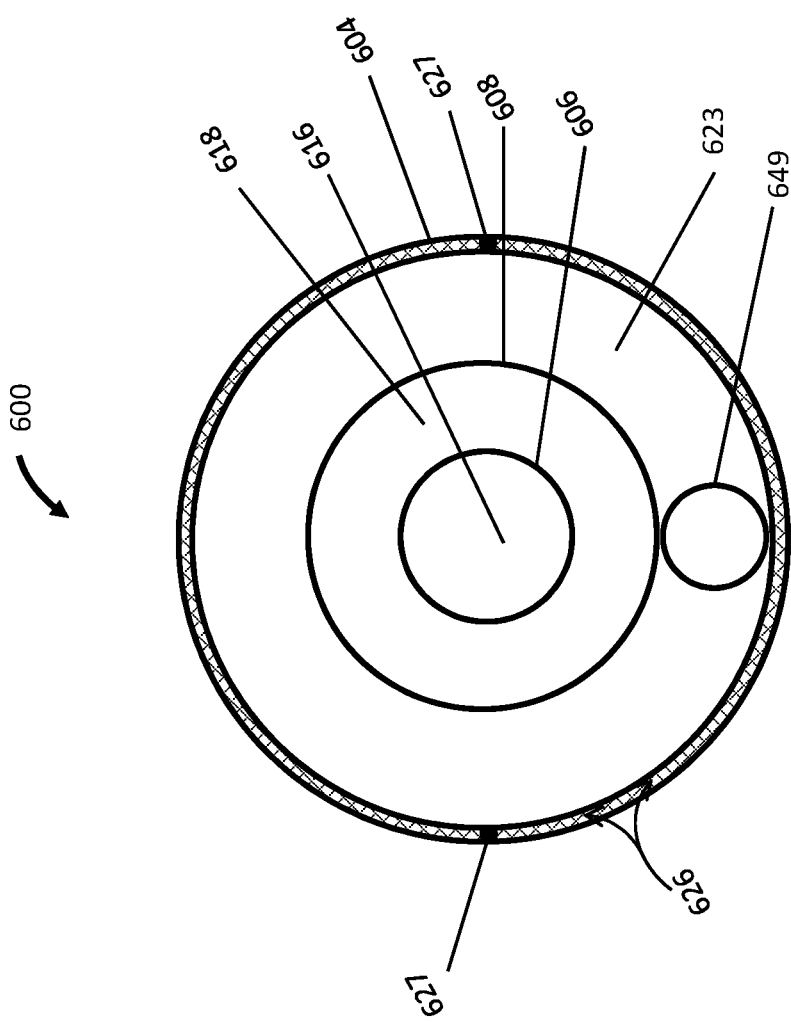
FIG. 8 is a cross sectional illustration of a cryoablation catheter device, according to an embodiment of the invention.

As best shown in FIG. 8, the device 600 includes a catheter shaft 604. Within catheter shaft 604, a cryogen supply line 606 is provided, having a lumen 616 therein. Cryogen supply line 606 may be substantially concentrically surrounded within catheter shaft 604 by a cryogen return line 608 having a lumen 618 therein, such that cryogen supply line 606 is disposed within cryogen return lumen 618. Cryogen return line 608 is disposed within catheter shaft 604, again in a substantially concentric arrangement. The cross sectional diameter of catheter shaft 604 is substantially greater than the cross sectional diameter of return line 608, leaving a gap circumferentially surrounding return line 608 within catheter shaft 604. This gap, between the inner wall of the catheter 604 and the outer wall of the return line 608, serves as insulating lumen 623, which provides thermal insulation to return line 608. Insulating lumen 423 is similar in structure and function to insulating lumen 423 (FIG. 4C).

As shown in FIG. 8, device 600 may also include an accessory injection tube 649, running substantially parallel to return line 608, supply line 606, and catheter shaft 604. Accessory injection tube 649 may be disposed within insulating lumen 623, such that it is within catheter shaft 604 but outside of return line 608. As shown in, e.g., FIGS. 6-7, accessory injection tube 649 may run the length of the device and may terminate at a distal end at an exit portal 647 in needle tip probe 602. Accessory injection tube 649 and exit portal 647 may be used in combination to deliver various treatment agents, e.g., anticancer agents, in conjunction with (i.e., any one or more of before, during, or after) an ablation procedure. Accessory injection tube 649 is similar in structure and function to the accessory injection tubes 449 (FIGS. 4A-B) and 557 (FIG. 5), and exit portal 647 is similar in structure and function to exit portal 447 (FIGS. 4A-B).

As previously described, device 600 includes a cryogen supply line 606, which supplies liquid cryogen to the distal tip of needle tip probe 602. As shown in, e.g., FIGS. 6-7, cryogen supply line 606 extends in a distal direction further than return line 608, such that supply line 606 extends distally further into needle tip probe 602 than its concentrically surrounding return line 608. Liquid or gas form cryogen is supplied through supply line 606 to needle probe tip 602, where it contacts inner surface 648 of needle probe tip 602. Heat exchange occurs across the surface of needle probe tip 602 between the cryogen within needle probe tip 602 and the target tissue, resulting in cryoablation, or tissue destruction, of tissue in contact with the ablation zone 622 of needle probe tip 602. Cryogen is then removed from needle tip probe 602 via return line 608.

The devices of FIGS. 6-14 are designed to be compatible with a number of cryogens, operating temperatures, and pressures. For exemplary proposes these cryogens may include argon, carbon dioxide, nitrous oxide, nitrogen gas, liquid nitrogen, pressurized and mixed phase cryogens, dual phase cryogens, propane, critical and super critical nitrogen, and others. Cryogen input operating pressures can range from about 50 psi to about 10,000 psi, and more commonly from about 1,000 psi to about 4,000 psi. Depending on the procedure and other parameters, cryogen operating temperatures within the needle tip probe 602 may typically range from about −70° C. to about −210° C. during operation, once cryogen flow to the ablation zone 622 has stabilized during operation. Various devices and methods for supplying cryogen to device 600 may be used, such as, e.g., those described in U.S. Pat. No. 9,089,316 and U.S. application Ser. No. 14/687,449, which are incorporated by reference herein as though fully set forth.

For delivery and return of the cryogen to the ablation zone 622 at the tip of the needle tip probe 602, a series of cryogen supply:return volume (e.g. cross sectional area of the tubing) ratios can be used in a coaxial configuration to provide optimal flow and heat extraction rates in the ablation zone 622 while minimizing choking flow created by back pressure. For example, the supply:return volume ratio may range from 1:1, 1:1.5; 1:2; or greater. As an example, the inner diameter of supply line 606 may be between about 0.33 mm and 1.5 mm, and the inner diameter of return line 608 may be between about 0.63 mm to 4.5 mm Determination of the desired supply:return volume ratio must include accounting for the internal diameter and the outer diameter (wall thickness) of the supply line 606 in relation to the inner diameter of the return line 608. This 1:1 or greater supply to return ratio (cross sectional area and/or volume) applies similarly to the ablation zone 622 within the probe tip 602.

Catheter shaft 604 itself, shown in cross section in FIG. 8, may be made of a flexible polymer material, and may range in diameter from, e.g., about 2 mm to about 10 mm, and in length from about 0.5 m to about 1.5 m. For example, an illustrative catheter shaft 604 may have a diameter of 3 mm and a length of 1 m, although larger and smaller diameters are also contemplated. In various embodiments, device 600 may further include deflection wires 627 embedded within the wall of catheter shaft 604 (as shown in FIG. 8) or adjacent the walls of catheter shaft 604, for use in directing and steering the needle probe tip 602 during use. Deflection wires 627 are similar in structure and function to deflection wires 427 (FIGS. 4A-C). The catheter shaft 604 may also include heating elements 626, which may also be embedded within the walls of catheter shaft 604. Heating elements 626 may be, e.g., resistance wires or other thermal insulation components to prevent unwanted freezing along catheter shaft 604. Heating elements 626 are similar in structure and function to heating elements 426 (FIGS. 4A-C).

Figure 9:
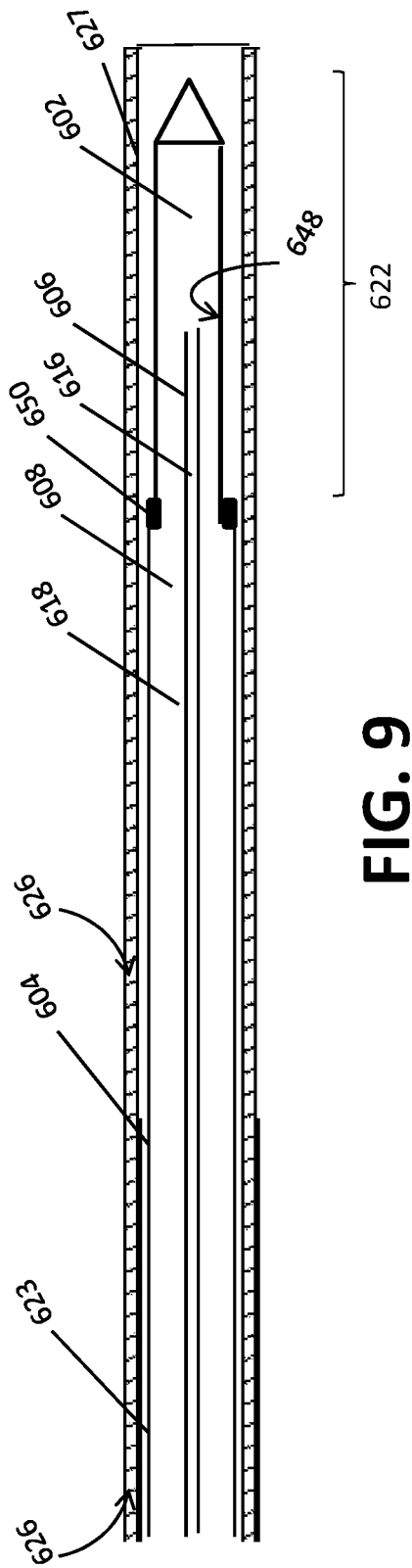
FIGS. 9-10 are illustrations of a device according to an embodiment of the invention, in the extended and retracted positions, respectively, including a needle-tip probe affixed to an inner wall of the cryogen return line, in an extended position.
Figure 10:
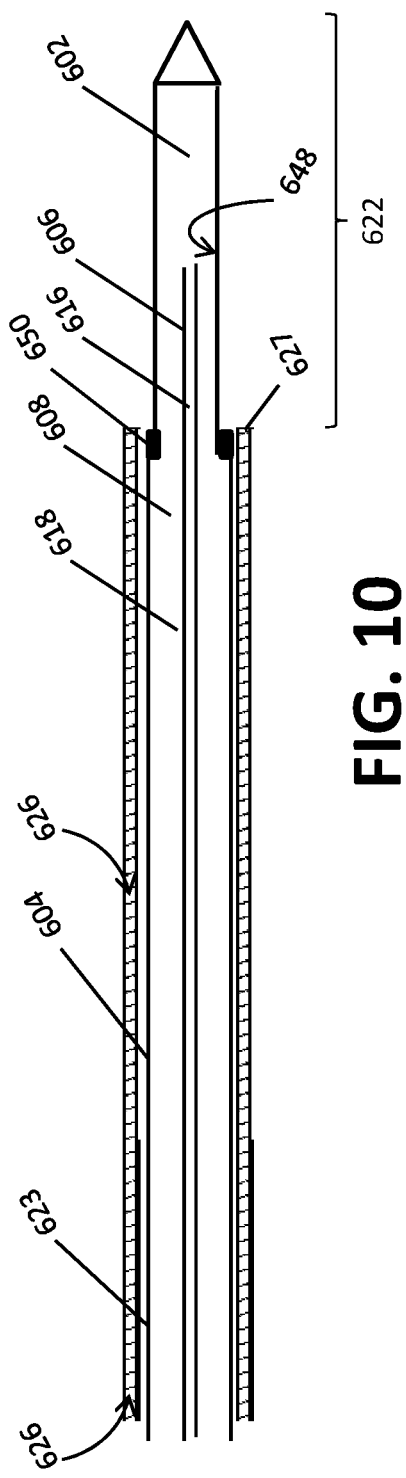

As shown in the embodiments of FIGS. 6-7, the needle-tip probe 602 may be affixed at joint 650 to the outer wall of return line 608. In other embodiments, as shown in FIGS. 9-10, the needle-tip probe 602 may be affixed at joint 650 to the inner wall of the return line 608. Regardless of whether needle-tip probe 602 is affixed to the inner wall or outer wall of return line 608, when device 600 is in the extended position as shown in FIGS. 6 and 9, the catheter shaft 604 is in the forward position and covers the distal tip of the needle-tip probe 602. When in the retracted position (as illustrated in FIGS. 7 and 10), the catheter shaft 604 is retracted and the distal tip of the needle tip probe 602 is exposed (FIGS. 7 & 10).

As shown in FIGS. 11-14, in some embodiments, return line 608 may be contained within an insulating tube 660. In these embodiments, tube 660 may be disposed within the catheter shaft 604 such that it substantially concentrically surrounds return line 608. Tube 660 may be thermally insulated using any form of insulation such as, e.g., vacuum insulation. Tube 660 may be affixed to needle probe tip 602 at joint 650, so that its position is substantially fixed with respect to return line 608, but catheter shaft 604 may freely move in an axial and/or rotational direction around tube 660 as shown in FIGS. 11-12.

In some embodiments, as shown in FIGS. 13-14, needle probe tip 602 may also include insulation 662 thereon. Insulation 662 may either be an integrally formed with needle probe tip 602, or may be a separate member applied over the proximal end of needle tip probe 602, such as a band of insulation that concentrically surround the proximal end of needle tip probe 602. In embodiments in which insulation 662 is applied over the proximal end of needle tip probe 602, it may be affixed at joint 663 via, e.g., epoxy, glue, solder, welding, brazing or any other method suitable for securing the insulation 662 to needle tip probe 602, as will be appreciated by one of skill in the art. In either event, a lumen 664 is provided within insulation 662, through which supply line 606 extends distally. Insulation 662 may be about 1 cm to about 20 cm in length, depending on the dimensions of needle tip probe 602. At the distal end of the insulation 662, needle tip probe 602 includes no insulation. This distal, uninsulated portion of needle tip probe 602 is the ablation zone 622.

The combination of the proximal portion of needle tip probe 602 that includes insulation 662, and the uninsulated distal end of needle tip probe 602 that forms ablation zone 622, restricts tissue freezing to the distal tip of needle tip probe 602. Insulation 662 prevents freeze damage to tissue adjacent to the proximal end of needle tip probe 602. This allows insertion of the ablation zone 622 into, and destruction of tissue targets anywhere within a tissue or organ without damaging non-targeted tissues adjacent to the insulation 662.

Insulation 662 may be any of a number of types of thermal insulation including but not limited to a permanent vacuum sleeve, drawing of an active vacuum, an air gap lumen, low thermal capacity material, a gas lumen, and active thermoelectric heating. In various embodiments, any of the forgoing types of thermal insulation may be used to provide insulation for catheter shaft 604 (FIGS. 6-14) and/or insulating tube 660 (FIGS. 11-14) in addition to insulation 662.

C. Cryoablation Catheter with Insulated Catheter Shaft

Figure 15:
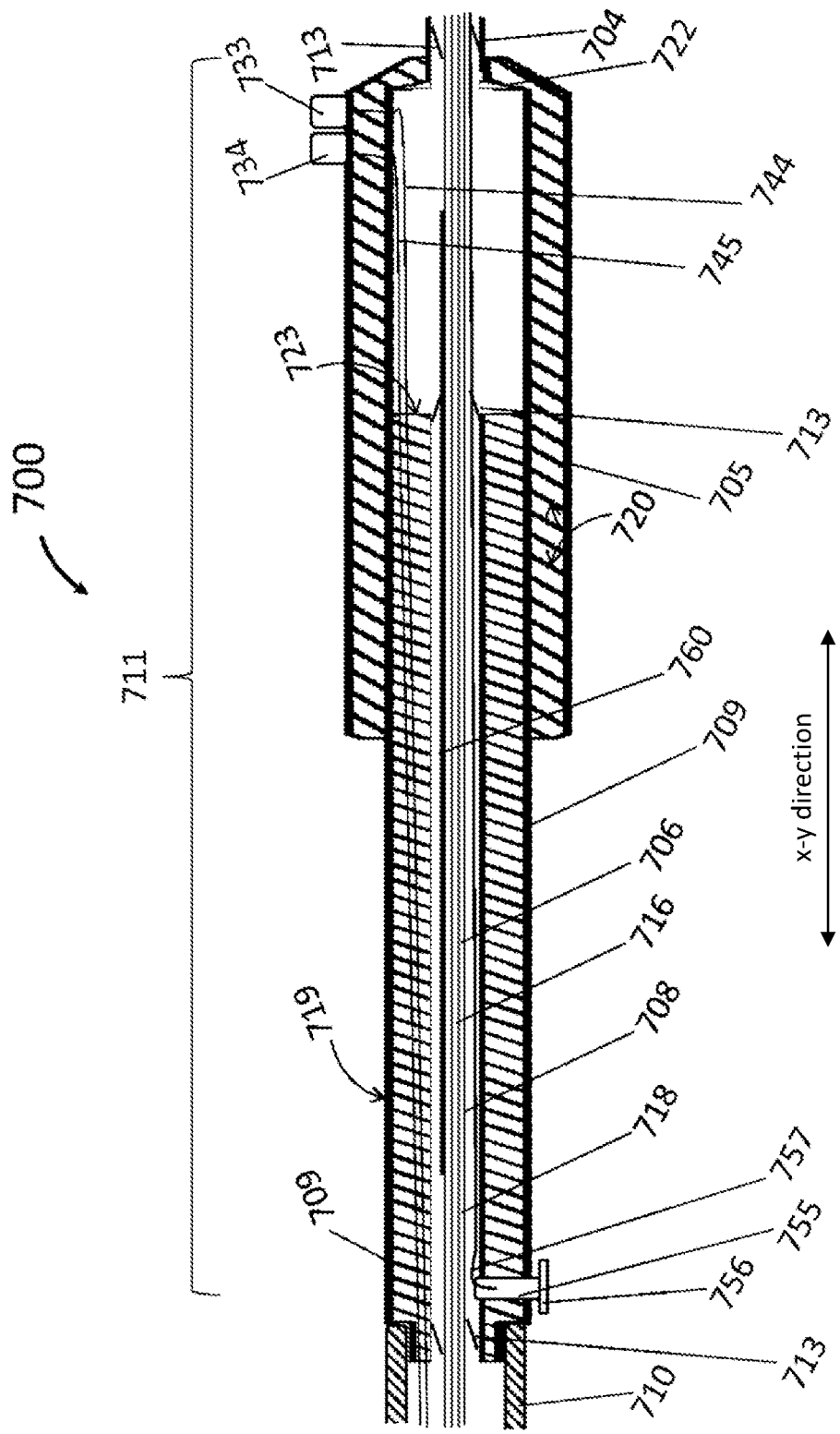
FIG. 15 is an embodiment of the invention with an internal view of the components in the handle portion depicting the return tube and catheter affixed to various locations within the handle.

Turning to FIG. 15, an embodiment of the invention as shown illustrates a section of the endoscopic ablation catheter apparatus 700. Depicted is the umbilical 710 attached to the retraction guide 709. Within the retraction guide, flexible return line 708 is affixed to the proximal and/or distal ends of the retraction guide 709 within the handle 705 by adhesives 713. Adhesives 713 may be epoxy, cyanoacrylate adhesives, or other medical grade superglue. The handle 705 attaches to a catheter shaft 704 at a distal end of the apparatus 700 such that the return line 708 can be moved in the x-y direction along the longitudinal axis in relation to the catheter 704 as desired by the user. The handle 705 surrounds the catheter 704 and retraction guide 709 to form an integrated handheld portion 711. The handheld portion 711 may also incorporate heating elements 720 to protect the user from cryo-temperatures generated within the device. As illustrated here, an internal forward stop 722 allows the handle 705, catheter 704 and return line 708 to move back and forth along the longitudinal axis, synchronously, a pre-determined distance such that the handle covers a portion of the retraction guide 709. A reverse stop 723 of the retraction guide 709 allows the handle 705, catheter 704 and return line 708 to be pushed forward (i.e., distally) a pre-determined distance thereby causing the distal end of the return line 708 and probe tip (not pictured) to emerge from the distal end of the catheter 704 (not shown). Distances can be indicated at, e.g., 0.5 cm markings on the handle portion 711 to allocate the desired protraction and retraction of the return line 708 in relation to the catheter 704. Any desired increment, however, may be designated and marked, e.g., centimeters, millimeters, fractions of an inch, etc. The markings allow the user to customize movement of the return line 708 to a desirable location thereby allowing a record of the length of return line or probe tip exposed. Additionally, in some embodiments the return line may be the limiting factor so as to designate the distance the handle is permitted to retract in which the return line is not permitted to move beyond the larger diameter of the retraction guide. Additionally in some embodiments, the handheld portion 711 may also include a reinforcement tube 760. Reinforcement tube 760 is affixed on an inner surface thereof to the outer surface of the return line 708. Reinforcement tube 760 may also be affixed on the outer surface thereof to the inner surface of the retraction guide 709 (not shown). The reinforcement tube 760 may be contained within and may protrude at either or both the distal or proximal end from the retraction guide 709. This reinforcement tube 760 may provide additional support to the return line 708 during actuation of the handheld portion 711.

As illustrated, the supply line 706 has the internal lumen 716 for delivery of cryogenic fluid to the probe tip. Return line 708 is positioned circumferentially about the supply line 706 to form the cylindrical lumen 718 disposed longitudinally within the supply line 706 throughout the length of the endoscopic cryoablation apparatus. Further, on/off controls 733 and 734 provide electrical connection 744 and 745, respectively, to allow the user to turn on/off the cryogen source, thaw, and/or heating elements 720. Other controls may be implemented to control gaseous discharge from the cryo-return lines, heating mechanisms throughout the length of the apparatus, temperatures adjustments, thermal monitoring, and visualization, among other features. Automated operation of the apparatus may also be incorporated with the use of software-based systems. In one aspect, automated control mechanisms also operate the sheath, individually or in combination with the handle. Further, the controls of the invention can be motorized for gradual precise positioning, as well as computerized to operate protraction and retraction of the sheath in synchrony with the handle. Any number of components of the invention may be motorized, computerized, and programmed as desired. Where the endoscopic cryocatheter is programmed, specific patient parameters may be integrated with a software program to facilitate placement of the probe tip, temperature adjustments, and treatment durations.

In another aspect, as shown in FIG. 15, the endoscopic cryoablation catheter 700 may also comprise an injection channel 755, access port 756, and accessory tube 757 for administering drugs, adjuvants, and therapeutic agents at the target tissue site. The access port 756 may be a rigid twist lock within the handheld portion 711, but may also be a flexible tube to allow introduction of an agent via a syringe or similar mechanism. The access port 756 may be positioned on the outer wall 719 of the retraction guide 709, or anywhere in the handle portion 711 or along the length of the umbilical 710 or catheter shaft 704. The injection channel 755 allows entry of the agent into the accessory tube 757; the accessory tube 757 then runs longitudinally along the length of the catheter shaft 704 to the distal end at the probe tip. An exit portal (not depicted here) within the probe tip seals a terminal portion of the accessory tube 757 to the probe tip to prevent any cryogen leaking from the probe tip. The accessory tube 757 is configured adjacent to the return line 708, within or along the catheter shaft 704 to allow for the introduction of additional adjuvants and agents as used in therapies such as chemotherapy, gene therapy, hormone and vitamin therapies. Such agents may include chemotherapeutic agents, gene therapy vectors, hormones, vitamins, pro-apoptotic or anti-apoptotic agents, and clotting agents, among others. The agents may be introduced at any stage of the procedure, including before, during, or after an ablation procedure. This accessory channel 757, along with the injection channel 755 and access port 756 can also be utilized for the introduction of biopsy needle apparatus, aspiration of fluid or tissue, or other device as desired. Additionally, the introduction of other ablative devices such as RF, high frequency ultrasound (HiFU), laser, or other ablative energies can be introduced. These channels within or along the endoscopic cryocatheter allow for the application of multiple treatment modalities to more effectively destroy the target tissue.

Turning to FIGS. 16-24, these figures illustrate various embodiments in which, in contrast with the foregoing embodiments, needle-tip probe 802 is affixed at joint 850 to the distal end of return line 808 within catheter shaft 804. Joint 850 may use adhesive such as, e.g., glue, to adhere needle tip probe 802 to return line 808. Within the catheter shaft there is an insulative tube 870 which is affixed to catheter shaft 804 at the distal end of the catheter shaft 804 at joint 871. A similar joint 871 may also affix the catheter 804 to the insulative tube 870 at the proximal end of the catheter shaft (not shown). As illustrated in cross section in FIG. 20, the circumferential space between the catheter shaft 804 and insulative tube 870 creates an insulative lumen 872 along the length of the catheter 804 thereby creating an insulated catheter shaft. The insulative tube 870 is fixed in its axial position in relation to the catheter 804. The insulation in the insulative lumen 872 may include, but is not limited to, a permanent vacuum sleeve, drawing of an active vacuum, an air gap lumen, low thermal capacity material, a gas lumen, and active thermoelectric heating.

In these embodiments, needle-tip probe 802 is axially moveable in relation to the surrounding catheter shaft 804, insulative tube 870, and insulative lumen 872. Catheter shaft 804, insulative tube 870 and insulative lumen 872 may also be rotationally movable around needle-tip probe 802 and return line 808.

Aside from the absence of the sheath and the inclusion of the insulative tube 870 and insulative lumen 872, and differences in actuation of needle probe tip 802 and return line 808 with respect to catheter shaft 804, device 800 of FIGS. 16-24 operates substantially similarly to devices 100/400/500/600 of FIGS. 1-14, respectively. Specifically, any feature described above with respect to device 100/400/500/600 may also be combined with device 700 of FIG. 15 and device 800 of FIGS. 16-24. Any such combinations are omitted only in the interest of brevity.

As best shown in FIG. 16, the device 800 includes catheter shaft 804. Within catheter shaft 804, cryogen supply line 806 is provided, having lumen 816 therein. Cryogen supply line 806 may be substantially circumferentially, e.g., concentrically surrounded within catheter shaft 804 by cryogen return line 808 having lumen 818 therein, such that cryogen supply line 806 is disposed within cryogen return lumen 818. Cryogen return line 808 is disposed within insulative tube 870 which is disposed within catheter shaft 804, again in a circumferential, e.g., substantially concentric arrangement. The cross sectional inner diameter of catheter shaft 804 is substantially greater than the cross sectional outer diameter of insulative tube 870 leaving a gap circumferentially surrounding insulative tube 870 within catheter shaft 804. The gap between the inner wall of the catheter 804 and the outer wall of the insulative tube 870 creates an insulative lumen 872, which provides thermal insulation to return line 808. Insulative lumen 872 is similar in structure and function to insulating lumen 423 (FIG. 4C) and 623 (FIGS. 6-14). The cross sectional diameter of insulative tube 870 is greater than the cross sectional outer diameter of return line 808, leaving a gap circumferentially surrounding return line 808 within insulative tube 870 thereby allowing the return line 808 to move freely within the insulative tube 870.

FIG. 16 illustrates the needle-tip probe 802 and return tube 808 in a retracted position within the catheter 804 and insulative tube 870, whereas FIG. 17 illustrates the needle-tip probe 802 and return line 808 in an extended position, in which the needle tip probe 802 and return line 808 extend distally out of the catheter 804 and insulative tube 870. The distance the needle-tip probe can extend beyond the distal end of catheter 804 varies and can be determined by a user through actuation of the handle mechanism as described relative to FIGS. 5 and 15.

As shown in FIG. 18, device 800 may also include an accessory injection tube 849, running substantially parallel to return line 808, supply line 806, insulative tube 870 and catheter shaft 804. Accessory injection tube 849 may be disposed within insulative lumen 872, such that it is within catheter shaft 804 but outside of insulative tube 870. Alternatively, the accessory injection tube 849 may be disposed within the insulative tube 870 but outside the return line 808. As shown in, e.g., FIGS. 18-19, accessory injection tube 849 may run the length of the device and may terminate at a distal end at an exit portal 847 in needle tip probe 802. The accessory injection tube 849 may also run the length of the device and may terminate at a distal end at an exit portal at the distal end of the catheter 804 (not shown). Accessory injection tube 849 and exit portal 847 may be used in combination to deliver various treatment agents, e.g., anti-cancer agents, in conjunction with (i.e., any one or more of before, during, or after) an ablation procedure. Accessory injection tube 849 is analogous in structure and function to the accessory injection tubes 449 (FIGS. 4A-B), 557 (FIG. 5) and 649 (FIGS. 6-7 and 11-14), and exit portal 847 is analogous in structure and function to exit portal 447 (FIGS. 4A-B) and 647 (FIGS. 6-7 and 11-14).

As previously described, device 800 includes a cryogen supply line 806, which supplies liquid cryogen to the distal tip of needle tip probe 802. As shown in, e.g., FIGS. 16-17, cryogen supply line 806 extends in a distal direction further than return line 808, such that supply line 806 extends distally further into needle tip probe 802 than its circumferentially surrounding return line 808. Liquid or gas form cryogen is supplied through supply line 806 to needle probe tip 802, where it contacts inner surface 848 of needle probe tip 802. Heat exchange occurs across the surface of needle probe tip 802 between the cryogen within needle probe tip 802 and the target tissue, resulting in cryoablation, or tissue destruction, of tissue in contact with the ablation zone 822 of needle probe tip 802. Cryogen is then removed from needle tip probe 802 via return line 808.

The devices of FIGS. 16-24 are designed to be compatible with a number of cryogens, operating temperatures, and pressures. For exemplary proposes these cryogens may include argon, carbon dioxide, nitrous oxide, nitrogen gas, liquid nitrogen, pressurized and mixed phase cryogens, dual phase cryogens, propane, critical and super critical nitrogen, and others. Cryogen input operating pressures can range from about 50 psi to about 10,000 psi, and more commonly from about 1,000 psi to about 4,000 psi. Depending on the procedure and other parameters, cryogen operating temperatures within the needle tip probe 802 may typically range from about −70° C. to about −210° C. during operation, once cryogen flow to the ablation zone 822 has stabilized during operation. Various devices and methods for supplying cryogen to device 800 may be used, such as, e.g., those described in U.S. Pat. Nos. 9,089,316 and 10,054,262, which are incorporated by reference herein as though fully set forth.

For delivery and return of the cryogen to the ablation zone 822 at the tip of the needle tip probe 802, a series of ratios of cryogen supply:return volume (e.g. cross sectional area of the tubing) can be used in a coaxial configuration to provide optimal flow and heat extraction rates in the ablation zone 822 while minimizing choking flow created by back pressure. For example, the supply:return volume ratio may range from 1:1, 1:1.5; 1:2; or greater. As an example, the inner diameter of supply line 806 may be between about 0.33 mm and 1.5 mm, and the inner diameter of return line 808 may be between about 0.63 mm to 4.5 mm Determination of the desired supply:return volume ratio must include accounting for the internal diameter and the outer diameter (wall thickness) of the supply line 806 in relation to the inner diameter of the return line 808. This 1:1 or greater supply to return ratio (cross sectional area and/or volume) applies similarly to the ablation zone 822 within the probe tip 802.

Figure 20:
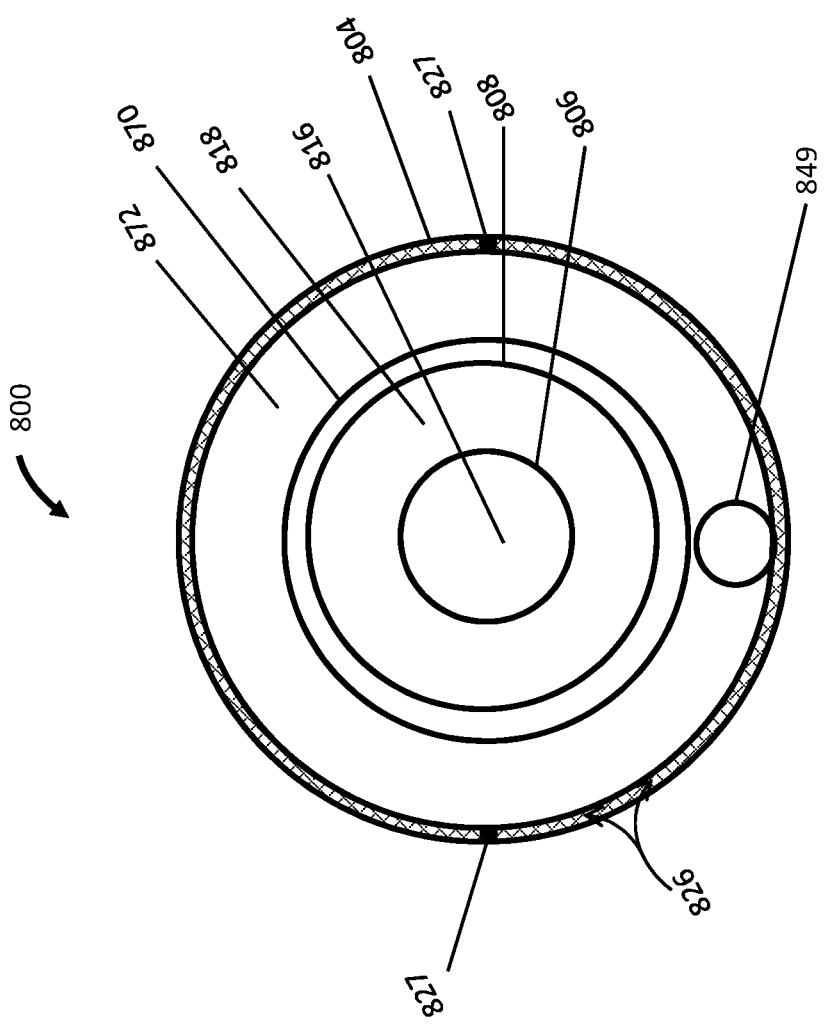
FIG. 20 is a cross sectional illustration of a cryoablation catheter device, according to an embodiment of the invention with an insulated catheter shaft.

Catheter shaft 804 itself, shown in cross section in FIG. 20, may be made of a flexible polymer material, and may range in diameter from, e.g., about 2 mm to about 10 mm, and in length from about 0.5 m to about 1.5 m. For example, an illustrative catheter shaft 804 may have a diameter of 3 mm and a length of 1 m, although larger and smaller diameters are also contemplated. In various embodiments, device 800 may further include deflection wires 827 embedded within the wall of catheter shaft 804 (as shown in FIG. 20) or adjacent the walls of catheter shaft 804, for use in directing and steering the needle probe tip 802 during use. Deflection wires 827 (FIGS. 16-24) are analogous in structure and function to deflection wires 427 (FIGS. 4A-C) and 627 (FIGS. 6-14). The catheter shaft 804 may also include heating elements 826, which may also be embedded within the walls of catheter shaft 804. Heating elements 826 may be, e.g., resistance wires or other thermal insulation components to prevent unwanted freezing along catheter shaft 804. Heating elements 826 are analogous in structure and function to heating elements 426 (FIGS. 4A-C) and 626 (FIGS. 6-14). The catheter shaft may also contain an insulative tube 870 between the inner wall of the catheter 804 and the outer wall of the return line 808 creating a insulative lumen 872.

As shown in the embodiments of FIGS. 16 and 17, the needle-tip probe 802 may be affixed at joint 850 to the outer wall of return line 808 as in FIGS. 11-12, joint 650. In other embodiments, similar to the manner shown in FIGS. 9 and 10, the needle-tip probe 802 may be affixed at joint 850 to the inner wall of the return line 808. Regardless of whether needle-tip probe 802 is affixed to the inner wall or outer wall of return line 808, when device 800 is in the catheter extended position as shown in FIGS. 16 and 18, analogous to FIGS. 6, 9, 11 and 13, the catheter shaft 804 is in the forward position and covers the distal tip of the needle-tip probe 802. When in the retracted position (as illustrated in FIGS. 17 and 19, and analogous to FIGS. 7, 10 and 14), the catheter shaft 804 is retracted and the distal tip of the needle tip probe 802 is extended beyond the end of the catheter 804. (FIGS. 17 and 19). Extension of the needle-tip probe 802 beyond the distal end of the catheter 804 may be accomplished by either retraction of the catheter 804 or extension of the return line 808 and needle-tip probe 802 in relation to one another.

As shown in FIGS. 16-24, in some embodiments, return line 808 may be contained within an insulative tube 870. In these embodiments, the insulative tube 870 may be disposed within the catheter shaft 804 such that it circumferentially, e.g., substantially concentrically surrounds return line 808. Insulative tube 870 may be thermally insulated using any form of insulation including but not limited to a permanent vacuum sleeve, drawing of an active vacuum, an air gap lumen, low thermal capacity material, a gas lumen, and active thermoelectric heating. Insulative tube 870 may be affixed to the inner wall of the catheter 804 at joint 871, so that its axial position is substantially fixed with respect to catheter 804, but catheter shaft 804 and insulative tube 870 may freely move in an axial and/or rotational direction in relation to the return line 808 and needle tip 802 as shown in FIGS. 16-24.

In some embodiments, as shown in FIGS. 21-24, needle probe tip 802 may also include insulation 862 thereon. Insulation 862 may either be integrally formed with needle probe tip 802, or may be a separate member applied over or within the proximal end of needle tip probe 802, such as a band of insulation that concentrically surrounds or is disposed within the proximal end of needle tip probe 802. In embodiments in which insulation 862 is applied to the proximal end of needle tip probe 802, it may be affixed at joint 863 via, e.g., epoxy, glue, solder, welding, brazing or any other method suitable for securing the insulation 862 to needle tip probe 802, as will be appreciated by one of skill in the art. In either event, a lumen 864 is provided within insulation 862, through which supply line 806 extends distally. Insulation 862 may be about 1 cm to about 20 cm in axial length, depending on the dimensions of needle tip probe 802. At the distal end of the insulation 862, needle tip probe 802 includes no insulation. This distal, uninsulated portion of needle tip probe 802 is the ablation zone 822.

The combination of the proximal portion of needle tip probe 802 that includes insulation 862, and the uninsulated distal end of needle tip probe 802 that forms ablation zone 822, restricts tissue freezing to the distal tip of needle tip probe 802. Insulation 862 prevents freeze damage to tissue adjacent to the proximal end of needle tip probe 802. This allows insertion of the ablation zone 822 into, and destruction of tissue targets anywhere within a tissue or organ without damaging non-targeted tissues adjacent to the insulation 862.

Insulation 862 may be any of a number of types of thermal insulation including but not limited to a permanent vacuum sleeve, drawing of an active vacuum, an air gap lumen, low thermal capacity material, a gas lumen, and active thermoelectric heating. In various embodiments, any of the forgoing types of thermal insulation may be used to provide insulation for catheter shaft 804 (FIGS. 16-24) and/or insulative tube 870 (FIGS. 20-24) in addition to insulation 862.

As shown in FIGS. 23-24, device 800 may also include an accessory injection tube 849, running substantially parallel to return line 808, supply line 806, insulative tube 870 and catheter shaft 804. Accessory injection tube 849 may be disposed within insulative lumen 872, such that it is within catheter shaft 804 but outside of the insulative tube 870. Alternatively, accessory injection tube 849 may be disposed within insulative tube 870, such that it is within insulative tube 870 but outside of the return line 808. Lastly, the accessory channel 849 may be disposed within the wall of the catheter 804. As shown in, e.g., FIGS. 23-24, accessory injection tube 849 may run the length of the device and may terminate at a distal end at an exit portal 847 in needle tip probe 802. Alternatively, accessory injection tube 849 may run the length of the device and may terminate at a distal end at an exit portal 847 at the distal end of the catheter 804 (not shown). Accessory injection tube 849 and exit portal 847 may be used in combination to deliver various treatment agents, e.g., anticancer agents, in conjunction with (i.e., any one or more of before, during, or after) an ablation procedure. Accessory injection tube 849 is analogous in structure and function to the accessory injection tubes 449 (FIGS. 4A-B), 557 (FIGS. 5 and 15), 649 (FIGS. 6-7) and 849 (FIGS. 18-19), and exit portal 847 is analogous in structure and function to exit portal 447 (FIGS. 4A-B), 647 (FIGS.

6-7) and 847 (FIGS. 18-19). In some embodiments the needle-tip probe 802 may also consist of alternate tip shapes including blunt tip, linear tip, balloon tip or lasso tip shaped ablation zones.

D. Uses of the Cryoablation Catheter Device

The device 100, 400, 500, 600, 700, 800 is designed to provide the physician with a tissue ablation zone by freezing the target cancer or unwanted tissue while reducing collateral damage to surrounding non-targeted areas. The cryoablation device allows for more effective, reproducible, and controllable tissue ablation to treat diseased tissue. Further, the materials designated for manufacturing the apparatus of the invention integrate stainless steel cryo-supply lines, polyamide return lines as configured for cryo-temperatures, and any combination thereof. The umbilical is composed of flexible materials as known in the art but may be modified to include plastics and polymeric combinations that are useful in the field of medicine.

One embodiment of the cryoablation catheter incorporates the use of an endoscopic ultrasound (EUS) device such that the endoscopic catheter apparatus 100 can be passed through an accessory channel of an existing EUS device. Once the endoscopic catheter is inserted and manipulated within proximity of a tissue site for treatment, the sheath is retracted to expose the needle cryoablation probe; and the probe is inserted into the target tissue under ultrasound or other means of visualization.

For exemplary purposes and not limitation, the endoscopic ablation catheter of the invention is utilized in ablating pancreatic tumor tissue. The catheter is inserted through an accessory port of the ultrasound endoscope through the stomach. Once positioned in the stomach nearest the adjacent pancreatic treatment area, the sheath is retracted and the probe inserted through the stomach wall into the pancreatic tumor, simultaneously. The steps of retracting the sheath and then inserting the probe may occur in two separate steps as selected during treatment. The cryoprobe is then activated to freeze the target tissue such that the distal-most portion of the needle-tip probe creates an ablation zone. The intermediary remainder of the needle that penetrates the stomach wall does not freeze and does not damage extraneous tissue outside the ablation zone. When freezing is completed, the tissue is allowed to thaw, either passively or actively via the integrated heating element within the probe. The thaw enables removal of the probe from the frozen tissue mass without an extensive time delay. In this regard, the integrated heating element within the tip of the cryoprobe can be activated to accelerate tissue thawing or probe release from the tissue (rapid release). In addition to thawing the tissue, elevated temperatures can be achieved with the heating elements to ablate selected tissue, thereby allowing for the dual application of cryoablation and hyperthermic (heat) ablation at a target tissue site.

In another aspect, the cryocatheter is inserted as described for a specified cryo-treatment while a chemotherapeutic agent, a gene therapy agent or vector, a cell therapy agent, radiation, a vitamin, an anti-apoptotic or pro-apoptotic agent, a clotting agent or other desired agent is administered to the target tissue region via one or more intergraded tubes/channels. The agents can be injected manually or automated with agent introduction points at the catheter handle or console. Addition of adjuvant or agent may occur prior to, during, or following the cryo-treatment procedure. Furthermore, collection of tissue biopsies or fluid/tissue aspiration can be accomplished through the introduction of a biopsy needle or application of an aspiration vacuum (vacuum, pump, suction, syringe or other means of aspiration) via one of the accessory channels.

As embodied in the invention, the device and procedure utilizes freezing in tandem with an endoscopic ultrasound device or any other type of endoscope. Additionally the device and procedure can be combined with any other ablation or anti-cancer therapy through the intergraded accessory tubes/channels within the cryocatheter assembly. The ECC device represents a significant advantage in the treatment of pancreatic and gastrointestinal cancers or other diseases.

Such benefits encompassed by the technology include the ability of the endoscopic compatible cryoablation probe/catheter to generate an ultracold cryo-lesion, enhancing destruction of cancer cells while minimizing side effects, and with the ability to rapidly ablate larger areas of pancreatic tissue. Furthermore, one embodiment of the invention utilizes a method for applying cryoablation via endoscopic access to the target tissue which can include the pancreas, intestine, or other portion of the gastrointestinal track. In another embodiment variations of the device can also be used with other ultrasound or non-ultrasound based endoscope variants, including cystoscopes ureteroscopes, colorectal scopes, laryngeal scopes, etc. (i.e., endoscopes) for the treatment of disease including cancerous and noncancerous lesions of the liver, stomach, colon, rectum, intestine, bladder, uterus, vagina, kidney, urethra, ureters, lungs, esophagus, etc.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth here-below not be construed as being order-specific unless such order specificity is expressly stated in the claim.

The invention claimed is:

1. A cryoablation device comprising:
   a catheter shaft;
   a cryogen return line disposed within the catheter shaft;
   a cryogen supply line disposed within the cryogen return line, such that the cryogen supply line, the cryogen return line, and the catheter shaft are all substantially coaxial;
   a needle tip probe disposed at a distal end of the cryogen return line, wherein the cryogen supply line extends in a distal direction beyond a distal end of the cryogen return line and into the needle tip probe;
   an insulating tube disposed circumferentially around the cryogen return line and within the catheter shaft;
   an insulating lumen circumferentially disposed around the cryogen return line, between an inner diameter of the catheter shaft and an outer diameter of the insulating tube,
   wherein a position of the insulating tube is axially and rotationally fixed relative to the catheter shaft, and wherein a position of the needle tip probe and the cryogen return line is axially and rotationally movable with respect to the insulating tube and the catheter shaft; and
   a heating element embedded within a wall of the catheter shaft.

2. The cryoablation device of claim 1, wherein the insulating lumen further comprises a vacuum sleeve, an actively drawn vacuum, an air gap, or a low thermal conductivity material.

3. The cryoablation device of claim 1, wherein the needle tip probe is affixed to an outer wall of the cryogen return line at the distal end of the cryogen return line.

4. The cryoablation device of claim 1, wherein the needle tip probe is affixed to an inner wall of the cryogen return line at the distal end of the cryogen return line.

5. The cryoablation device of claim 1, wherein the needle tip probe is affixed to the distal end of the cryogen return line using one of glue, epoxy, solder, welding, or brazing.

6. The cryoablation device of claim 1, wherein the needle tip probe further includes insulation affixed thereto and disposed on a proximal end thereof, and wherein the insulation disposed on the proximal end of the needle tip probe defines an ablation zone on a distal end of the needle tip probe for providing treatment.

7. The cryoablation device of claim 1, wherein a ratio of a volume of the supply line to a volume of the return line is 1:1, 1:1.5, or 1:2.

8. The cryoablation device of claim 1, wherein a ratio of a cross sectional area of the supply line to a cross sectional area of the return line is 1:1, 1:1.5, or 1:2.

9. The cryoablation device of claim 1, further comprising a deflection wire embedded within, or disposed adjacent to a wall of the catheter shaft.

10. The cryoablation device of claim 1, further comprising an accessory injection tube disposed within the catheter shaft, such that the accessory injection tube is parallel to the cryogen return line.

11. The cryoablation device of claim 10, further comprising an exit portal in the needle tip probe,
wherein the accessory injection tube terminates at a distal end thereof at the exit portal, and the exit portal is configured to deliver a treatment agent to a treatment site, or to remove a tissue or a fluid from the treatment site.

12. The cryoablation device of claim 10,
wherein the accessory injection tube is disposed within the insulating lumen.

13. The cryoablation device of claim 10, wherein the accessory injection tube is disposed within the catheter shaft, such that the accessory injection tube is contained within the wall of the catheter.

14. The cryoablation device of claim 10, further comprising an exit portal in the catheter or the insulating lumen,
wherein the accessory injection tube terminates at a distal end of the needle tip at the exit portal, and the exit portal is configured to deliver a treatment agent to a treatment site, or to remove a tissue or a fluid from the treatment site.

15. The cryoablation device of claim 1, wherein a proximal end of the catheter shaft is affixed to a distal portion of a handle and the return line is affixed to the proximal portion of the handle, and
wherein the catheter shaft, the handle and the return line are configured to allow simultaneous translational and rotational movement of the return line in relation to the catheter shaft to expose the needle tip probe and to cover the needle tip probe.

16. The cyroblation device of claim 15, wherein the handle retracts and protracts the catheter relative to the needle tip probe.

17. The cryoablation device of claim 15, wherein the handle comprises controls to operate one or more of cryogen delivery, temperature, and thermal insulation.

18. The cryoablation device of claim 1, further comprising one or more thermal elements in the needle tip probe.

19. A cryoablation device comprising:
a catheter shaft;
a cryogen return line disposed within the catheter shaft;
a cryogen supply line disposed within the cryogen return line, such that the cryogen supply line, the cryogen return line, and the catheter shaft are all substantially coaxial;
a needle tip probe disposed at a distal end of the cryogen return line, wherein the cryogen supply line extends in a distal direction beyond a distal end of the cryogen return line and into the needle tip probe;
an insulating tube disposed circumferentially around the cryogen return line and within the catheter shaft;
an insulating lumen circumferentially disposed around the cryogen return line, between an inner diameter of the catheter shaft and an outer diameter of the insulating tube, wherein a position of the insulating tube is axially and rotationally fixed relative to the catheter shaft, and wherein a position of the needle tip probe and the cryogen return line is axially and rotationally movable with respect to the insulating tube and the catheter shaft; and
an accessory injection tube disposed within the catheter shaft, such that the accessory injection tube is parallel to the cryogen return line.

20. A cryoablation device comprising:
a catheter shaft;
a cryogen return line disposed within the catheter shaft;
a cryogen supply line disposed within the cryogen return line, such that the cryogen supply line, the cryogen return line, and the catheter shaft are all substantially coaxial;
a needle tip probe disposed at a distal end of the cryogen return line, wherein the cryogen supply line extends in a distal direction beyond a distal end of the cryogen return line and into the needle tip probe;
a thermal element disposed within the needle-tip probe;
an insulating tube disposed circumferentially around the cryogen return line and within the catheter shaft; and
an insulating lumen circumferentially disposed around the cryogen return line, between an inner diameter of the catheter shaft and an outer diameter of the insulating tube, wherein a position of the insulating tube is axially and rotationally fixed relative to the catheter shaft, and wherein a position of the needle tip probe and the cryogen return line is axially and rotationally movable with respect to the insulating tube and the catheter shaft.

* * * * *